(12) United States Patent
Silver et al.

(10) Patent No.: US 7,179,461 B2
(45) Date of Patent: Feb. 20, 2007

(54) PLASMINOGEN ACTIVATOR TO PREVENT CORNEAL AND SUBEPITHELIAL HAZE AFTER LASER VISION CORRECTION SURGERY

(75) Inventors: David M. Silver, Bethesda, MD (US); Adrienne Csutak, Debrecen (HU); Andras Berta, Debrecen (HU); Jozsef Tozser, Debrecen (HU)

(73) Assignee: The Johns Hopkins University, Baltimore, MD (US)

( * ) Notice: Subject to any disclaimer, the term of this patent is extended or adjusted under 35 U.S.C. 154(b) by 431 days.

(21) Appl. No.: 10/398,677

(22) PCT Filed: Oct. 12, 2001

(86) PCT No.: PCT/US01/31849

§ 371 (c)(1),
(2), (4) Date: Apr. 9, 2003

(87) PCT Pub. No.: WO02/30444

PCT Pub. Date: Apr. 18, 2002

(65) Prior Publication Data

US 2004/0001821 A1  Jan. 1, 2004

Related U.S. Application Data

(60) Provisional application No. 60/240,264, filed on Oct. 13, 2000.

(51) Int. Cl.
*A61N 1/30* (2006.01)
*A61K 38/48* (2006.01)

(52) U.S. Cl. .................................. 424/94.63
(58) Field of Classification Search ............. 424/94.63
See application file for complete search history.

(56) References Cited

U.S. PATENT DOCUMENTS 6,737,075 B2* 5/2004 Karageozian ............... 424/427
2002/0119141 A1* 8/2002 Karageozian ............ 424/94.62

FOREIGN PATENT DOCUMENTS

DE  199 01 594 A1  8/2000
WO  WO 00/66139  11/2000

OTHER PUBLICATIONS

Csutak et al. 2004. INvestigative Opthalmology & Visual Science, May, vol. 45, No. 5, pp. 1329-1333.*
Plasminogen Activator Activity in Rabbit Tears after Excimer Laser Photorefractive Keratomy, A.Csutak, et al., IOVS, vol. 41, No. 4, pp. S69, Mar. 15, 2000.
The Effects of Topical Corticosteroids and Plasmin Inhibitors on Refractive Outcome, Haze, and Visual Performance after Photorefractive Keratectomy, David P.S. O'Brart et al., Ophthalmology, vol. 101, No. 9, Sep. 1994, p. 1565-1574.
Plasmin-and Plasminogen- Activator Inhibitors After Excimer Laser Photorefractive Keratectomy: New Concept in Prevention of Postoperative Myopic Regression and Haze, C.P. Lohmann, MD et al., Refractive & Corneal Surgery, vol. Jul./Aug. 1993.
Results and Complications in rTPA Treatment of the Anterior Segment of the Eye, K.U.Loffler et al.,Ophthalmologe, 94, p. 50-52, Jan. 1997, with English translation.

* cited by examiner

*Primary Examiner*—Jon Weber
*Assistant Examiner*—Kailash C. Srivastava
(74) *Attorney, Agent, or Firm*—Francis A. Cooch

(57) ABSTRACT

The present invention is directed to a method to prevent or reduce postoperative corneal subepithelial haze after excimer laser photorefractive keratectomy (PRK), laser in situ keratomileusis (LASIK) surgery. According to the method, a therapeutically effective amount of one or more plasminogen activators, most preferably urokinase (uPA), is administered topically to the surface of the affected eye at levels between 0.1 and 2,500 IU/ml, about eight to twelve times on the day of surgery, and four to eight times per day for about the next six to twelve days thereafter. The most preferred therapeutic amount is from about 0.1–1 IU uPA/ml, and also 1–10 IU/ml. Plasminogen activators that can be used in the inventions include urokinase, prourokinase, streptokinase and mutants thereof. The invention also covers topical ophthalmic compositions that include one or more plasminogen activators, most preferably uPA, to prevent or reduce postoperative corneal subepithelial haze.

18 Claims, 7 Drawing Sheets

Individual values of uPA in 77 human eyes following PRK

Mean uPA in humans for 71 eyes that healed without haze, and 8 eyes that developed postoperative haze Individual uPA values in contralateral human eyes that were not subjected to PRK Effect of treatment of rabbits with serine protease inhibitors on mean uPA levels following PRK Individual uPA values for 8 rabbit eyes not treated with
serine protease inhibitors following PRK Individual uPA values for 8 rabbit eyes treated with serine protease inhibitors following PRK Schematic diagram of the plasminogen activator to plasmin reaction system, showing the principle reaction in heavy lines, normal supporting reactions in light lines and damage mechanisms in dotted lines

PLASMINOGEN ACTIVATOR TO PREVENT CORNEAL AND SUBEPITHELIAL HAZE AFTER LASER VISION CORRECTION SURGERY

CROSS-REFERENCE TO RELATED APPLICATIONS

This application is the national stage filing and claims priority to PCT/US01/31849 filed on 12 Oct. 2001.

This application claims the benefit of prior filed co-pending U.S. provisional application No. 60/240,264, filed on Oct. 13, 2000.

BACKGROUND OF THE INVENTION

1. Field of the Invention

The present invention relates to pharmaceutical methods and products for use in the prevention or reduction of corneal subepithelial haze following laser vision correction surgery and other corneal injuries, especially photorefractive keratectomy (PRK) and laser in situ keratomileusis (LASIK).

2. Description of the Related Art

Laser refractive surgery is performed in increasing numbers on completely healthy eyes where adverse surgical effects are less acceptable than for diseased eye treatments. Complications attending laser refractive surgery, due to abnormal wound healing of the cornea, include central vision haze.

The cornea is responsible for two thirds of the refracting power of the eye, making it a candidate for surgical procedures aimed at refractive correction. The qualities of the wounds made by the ArF excimer laser suggested the concept of using such a laser to directly photoablate the cornea after removal of the epithelial layer. The effect is to reprofile the surface of the cornea, defining a new anterior radius of curvature, thereby altering the optical power of the cornea, a technique referred to as photorefractive keratectomy (PRK). The procedure is a reasonably safe, effective and predictable technique for correcting low to moderate myopia. The most frequently reported complications of PRK and any laser surgery, include glare, haloes, difficulty with night vision, decreased contrast sensitivity, transient increases in intraocular pressure, mild subepithelial haze and myopic regression [Chan T K, Ashraf M F, Azar D T. *Photorefractive keratectomy (PRK) outcomes and complications.* In: Azar D T, Steinert R F, Stark W J, eds. *Excimer Laser Phototherapeutic Keratectomy.* Baltimore, Md.: Williams & Wilkins; 1997:157–173; and Hadden O B, Ring C P, Morris A T, Elder M J. *Visual, refractive, and subjective outcomes after photorefractive keratectomy for myopia of 6 to 10 diopters using the Nidek laser. J Cataract Refract Surg* 1999;25:936–942.]

Laser refractive surgery is performed on the cornea of the eye using an excimer laser to correct myopia and other refractive errors. With photorefractive keratectomy (PRK), the whole corneal epithelium is removed and the excimer laser is applied to the Bowman layer and the anterior stroma. An ablation depth of approximately 10 microns corrects 1 Diopter of myopia. The resultant reshaping of the cornea alters its optical power. Alternatively, laser in situ keratomileusis (LASIK), uses a suction ring and a microkeratome to create a thin flap from the central corneal surface. The underlying stromal bed is treated with the excimer laser and the flap is repositioned. In the majority of PRK and LASIK cases, the refractive outcome is within ±0.5 Diopter of that intended. Re-epithelialization of the human cornea occurs usually within two to three days postoperatively. Post-laser surgery complications include excessive myopic regression and disturbances in corneal transparency (haze, cloudiness, scarring) due to irregularities in the wound healing process. Flap-related complications can also occur with LASIK. Efficacy outcomes in the long term are generally similar between the two procedures. Laser refractive surgery is elective and resembles cosmetic surgery since it is performed on completely healthy eyes. Complications in healthy eyes are even less acceptable than in diseased eyes. As the number of laser vision correction surgeries continues to increase exponentially, there is an even greater need to reduce complications such as subepithelial haze or cloudiness that can develop in some patients as a result of the procedure.

Corneal subepithelial haze or cloudiness following laser refractive surgery occurs as a result of the disrupted structure of the anterior stromal lamellae. Corneal haze is not apparent until a few weeks to a few months postoperatively. Its duration can be from weeks to months, with some occurrences lasting over a year. Its severity can be mild to strong. There is a wide variability in the reported prevalence of haze, but so far no effective remedy has been found to treat, reduce or prevent postoperative corneal haze.

There is a great need for a pharmacologically safe, effective drug that can prevent or reduce corneal haze after laser surgery and other corneal injuries. The present invention discloses such a drug and provides such a method.

SUMMARY OF THE INVENTION

The present invention describes a method of preventing or reducing postoperative corneal subepithelial haze following laser surgery by applying to the surface of the affected eye, a therapeutically effective amount of one or more plasminogen activators. The methods of the present invention are especially designed to prevent haze following photorefractive keratectomy (PRK) and laser in situ keratomileusis (LASIK), however the method prevents or reduces haze following any eye injury that is likely to cause haze including any photoablation of the cornea during ophthalmic surgery. The plasminogen activators for use in the present methods are urokinase, prourokinase, streptokinase or mutants thereof. In the most preferred embodiment, urokinase (uPA) is used alone.

In the most preferred embodiment, a therapeutically effective amount of plasminogen activator is applied to the surface of the eye in a physiologically acceptable carrier for ophthalmic use immediately following surgery and several times each day for up to twelve days following laser surgery, other ophthalmic surgery, eye injury or disease that is associated with the formation of haze. In one embodiment, the therapeutically effective amount of plasminogen activator is applied topically to the surface of the affected eye eight to twelve times on the day of surgery or injury starting immediately after surgery or injury, and four to eight times per day for the next six to twelve days thereafter. In a most preferred embodiment, plasminogen activator (most preferably urokinase) is applied about twelve times per day (for example, every hour during wakefulness) on day 1 starting immediately after surgery or injury, and five times per day (every two hours) on postoperative days 2–7. The therapeutically effective amount of plasminogen activator for use in the present methods is from about 0.1 to 2,500 IU/ml; most preferred is 0.1 to 1 IU/ml, with other embodiments including 1–10 IU/ml and 10–100 IU/ml.

The present invention is also directed to a topical ophthalmic composition for preventing or reducing corneal subepithelial haze following laser surgery, other ophthalmic surgery or resulting from an eye injury, containing a therapeutically effective amount of one or more plasminogen activators formulated in a physiologically acceptable carrier suitable for ophthalmic use. The plasminogen activator for use in the present compositions is preferably urokinase, but also includes, prourokinase, streptokinase or mutants thereof. The therapeutically effective amount of plasminogen activator in the composition is from about 0.1 to 2,500 IU/ml; most preferred is 0.1 to 1 IU/ml, with other preferred embodiments including 1–10 IU/ml and 10–100 IU/ml.

DETAILED DESCRIPTION

1. Definitions

Figure 1:
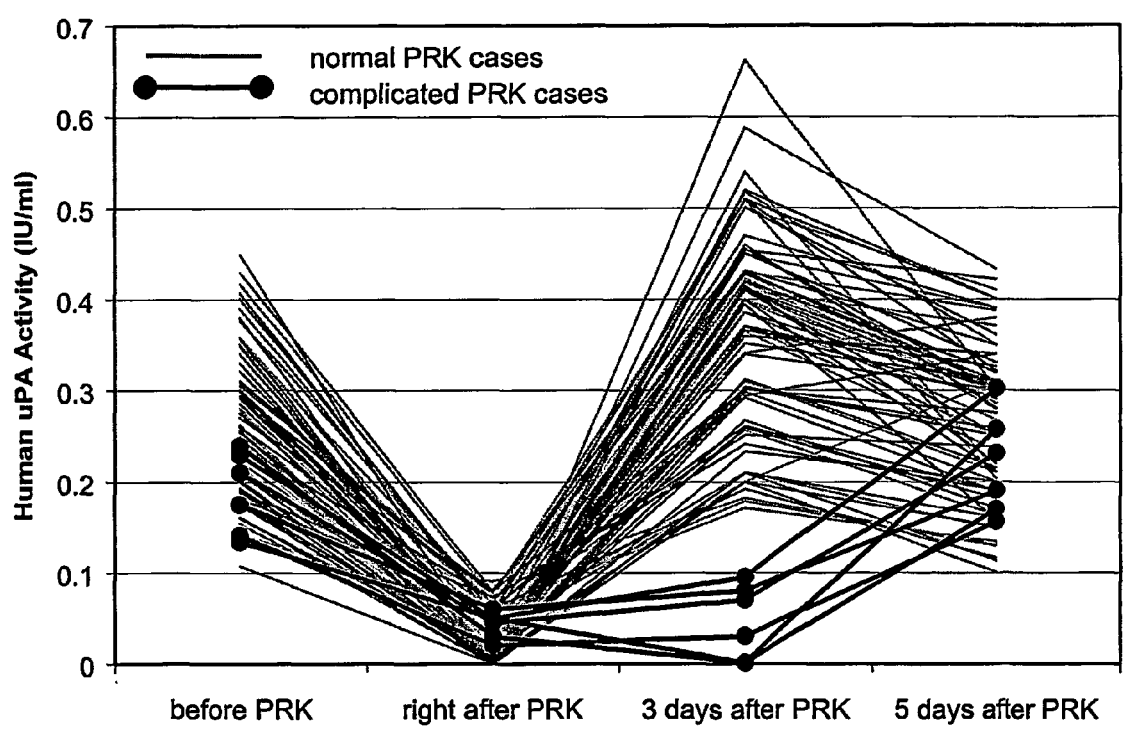
FIG. 1. Individual uPA activity levels before and after PRK on human eyes showing the cluster of individual values for eyes that healed normally (71/77) compared to the cluster of individual values for haze-complicated cases (6/77).

Adhesions as used herein means a fibrous band, exudate or structure thrown out on the surface of a serous membrane to which parts or opposing surfaces of a wound unite, connect or adhere. Corneal adhesions are distinct from haze in the eye.

Haze as used herein means corneal subepithelial haze, and it refers to disturbances in corneal transparency that makes vision hazy or cloudy. Haze is caused by the presence of unstructured collagen fibers excreted by activated keratocytes and affected extracellular matrix. When present, haze appears weeks to several months after laser eye surgery, usually during the first month, its intensity being highest during the postoperative 3–6 months. Haze can last up to a year before resolving.

Plasminogen activator as used herein means urokinase, prourokinase, streptokinase or mutants of any of these enzymes.

Urokinase as used herein means an enzyme originally found in the urine of mammals, including man, and of other vertebrates that is made by the parenchymal cells of the human kidney and functions as a plasminogen activator. It is used therapeutically as a thrombolytic (fibrinolytic agent). Commercial production of uPA includes a high molecular weight (MW=50,000–54,000) form predominant in urinary preparations and a low molecular weight (MW=31,300–33,000) form isolated from long-term cell cultures. uPA is identified with CAS registry #9039-53-6, Merck Index 10024 and EINACS #232-917-9. uPA is immunologically distinct from tPA.

Tissue plasminogen activator (tPA) as used herein means a plasminogen activator that was originally discovered in melanoma cells and is a product of vascular endothelial cells from a wide variety of tissues. tPA has a molecular weight (MW=64,000–70,000).

International Unit (IU) as used herein means that the plasminogen activator activity was standardized with the $1^{st}$ International Reference Preparation for uPA (66/46, National Institute for Biological Control, London, UK) using the chromogenic peptide substrate D-valyl-L-leucyl-L-lysine-p-nitroanilide (S-2251).

2. Description

The present invention provides a method for reducing or preventing haze (corneal subepithelial) following laser eye surgery (especially PRK and LASIK) by delivering a therapeutically effective amount of one or more plasminogen activators, most preferably urokinase, to the cornea preferably in the form of eye drops, immediately following surgery and for up to about the first twelve days after the procedure. Seven-day treatment is preferred. A therapeutically effective amount of plasminogen activator is from about 0.1–2,500 IU/ml. Most preferred is 0.1–1 IU/ml, with other preferred embodiments including 1–10 IU/ml and 10–100 IU/ml. The present invention is also directed to a topical ophthalmic composition for preventing or reducing corneal subepithelial haze following laser surgery and ophthalmic surgery or resulting from an eye injury, containing a therapeutically effective amount of a plasminogen activator in the range of 0.1–2,500 IU/ml, most preferred is 0.1–1 IU/ml, with other preferred embodiments including 1–10 IU/ml and 10–100 IU/ml, formulated in a physiologically acceptable carrier suitable for ophthalmic use. The plasminogen activators that can be used in the present methods and compositions include urokinase, urokinase mutants, prourokinase, prourokinase mutants, streptokinase and streptokinase mutants.

Excimer laser photorefractive keratectomy (PRK) is used for the correction of myopia, hyperopia and astigmatism. The excimer laser removes tissue through photoablative decomposition by delivering incident photon energy that is sufficient to break molecular bonds. Selective removal of tissue across the anterior surface results in a change in anterior corneal curvature. In the majority of cases the refractive outcome is within ±0.5 diopters of that intended, although there is some variation in the refractive outcome depending upon the preoperative refractive error. The surgical outcome is influenced by individual variability in wound healing and pharmacological intervention.

PRK complications include excessive myopic regression, haze, and either localized or diffuse dense scarring. [Lohmann C P, Gartry D S, Muir M K, Timberlake G T, Fitzke F W, Marshall J. *Corneal haze after excimer laser refractive surgery: objective measurements and functional implications. Eur J Ophthalmol.* 1991;1:173–180; Lohmann C P, Marshall J. *Plasmin- and plasminogen-activator inhibitors after excimer laser photorefractive keratectomy: new concept in prevention of postoperative myopic regression and haze. Refract Corneal Surg.* 1993;9:300–302.]

Histologically, haze is caused by the presence of unstructured collagen fibers excreted by activated keratocytes and affected extracellular matrix. When present, haze appears weeks after the PRK procedure, usually during the first month, its intensity being highest during the postoperative 3–6 months and it can last up to a year before resolving. In most cases haze eventually disappears after 6 months. The longest duration of post-operative haze is greater than 12 months. Complete re-epithelialization of the human cornea following laser surgery is usually completed 2–4 days after surgery, however, normal epithelial thickness is not observed until 6 months after surgery. [Lohmann et al. 1991,] Risk factors for haze have been suggested to include higher levels of myopic correction, noncompliance with postoperative steroid medication, steroid-induced intraocular pressure response, collagen vascular disease and other autoimmune diseases. [Chan T K, Ashraf M F, Azar D T. *Photorefractive keratectomy (PRK) outcomes and complications.* In: Azar D T, Steinert R F, Stark W J, eds. *Excimer Laser Phototherapeutic Keratectomy.* Baltimore, Md.: Williams & Wilkins; 1997:157–173; Hadden O B, Ring C P, Morris A T, Elder M J. *Visual, refractive, and subjective outcomes after photorefractive keratectomy for myopia of 6 to 10 diopters using the Nidek laser. J Cataract Refract Surg* 1999;25:936–942; Azar D T, Hahn T W, Khoury J M. *Corneal wound healing following laser surgery.* In: Azar D T, ed. *Refractive Surgery.* Stamford, Conn.: Appleton & Lange; 1997:41–61; Carones F, Fiore T, Brancato R. *Mechanical vs. alcohol epithelial removal during photorefractive keratectomy. J Refract Surg* 1999;15:556–562; and Siganos D S, Katsanevaki V J, Pallikaris I G. *Correlation of subepithelial haze and refractive regression 1 month after photorefractive keratectomy for myopia. J Refract Surg* 1999;15:338–342.]

A literature review indicates an occurrence of postoperative haze of various degrees of severity with LASIK on humans of about 8.7%. [Farah S G, Azar D T, Gurdal C, Wong J. *Laser in situ keratomileusis: literature review of a developing technique. J Cataract Refract Surg* 1998;24: 989–1006.] A frequency of occurrence of 8% has been observed for PRK. [Csutak A, Tözsér J, Békési L, Hassan Z, Berta A, Silver D M. *Plasminogen activator activity in tears after excimer laser photorefractive keratectomy. Invest Ophthalmol Vis Sci* 2000;41:3743–3747.] Reduction of the frequency or intensity of haze formation, even though it occurs in only a fraction of the surgical cases, is clinically significant.

Wound healing is regulated by two major systems that are controlled by activators and inhibitors. The first system is the plasminogen activator-plasmin system, which is involved in the degradation and removal of damaged extracellular matrix. Both urokinase and tissue-plasminogen activator (tPA) are involved in the first system. Mc Donnell P J. *Excimer laser corneal surgery: new strategies and old enemies. Invest Ophthalmol Vis Sci.* 1995;36:4–8; Gaster R N, Binder P S, Coalwell K, Berns M, McCord R C, Burstein N L. *Corneal surface ablation by 193 nm excimer laser and wound healing in rabbits. Invest Ophthalmol Vis Sci.* 1989; 30:90–98.] The second system is the activated keratocyte system, which is involved in the replacement of damaged collagen by synthesizing new collagen and the collagen matrix of glycosaminoglycans. This process is very important with respect to epithelial regrowth, but activating the synthetic activity of keratocytes can result in scar formation. The ulcerative mechanism with persistent epithelial defect is initiated if plasminogen activator is released with increased or prolonged activity. [Berman M, Leary R, Gage J. *Evidence for a role of the plasminogen activator—plasmin system in corneal ulceration. Invest Ophthalmol Vis Sci.* 1980;19:1204–1221; and Berman M. *Regulation of collagenase. Therapeutic consideration. Trans Ophthalmol Soc UK.* 1978;98:397–405; and Tözsér J, Berta A, Punyiczki M. *Plasminogen activator activity and plasminogen independent amidolytic activity in tear fluid from healthy persons and patients with anterior segment inflammation. Clin Chim Acta.* 1989;183:323–331.]

Urokinase-type plasminogen activator (uPA) is a serine protease found as a normal component of tear fluid, whose origin is conjunctival and corneal epithelial cells and whose concentration is influenced by biochemical transformations in the cornea. [Barlati S, Marchina E, Quaranta C A, et al. *Analysis of fibronectin, plasminogen activators and plasminogen in tear fluid as markers of corneal damage and repair. Exp Eye Res* 1990;51:1–9.] Tissue plasminogen activator (tPA) is also a normal component of tear fluid, produced in conjunctival cells, vessels of the conjunctiva and the lacrimal gland. [Tözsér J, Berta A, Punyiczki M. *Plasminogen activator activity and plasminogen independent amidolytic activity in tear fluid from healthy persons and patients with anterior segment inflammation. Clin Chim Acta.* 1989;183: 323–331. Hayashi K, Sueishi K. *Fibrinolytic activity and species of plasminogen activator in human tears. Exp Eye Res* 1988;46:131–137.] Normal corneal epithelial cells do not release plasminogen activator, but damage to the corneal epithelium causes keratocytes to release uPA, which converts plasminogen that is already present in the stroma, to plasmin. The plasmin in turn: (a) feeds back to fibroblast cells, inducing them to secrete more plasminogen activators; (b) activates the latent procollagenases to collagenases, which results in collagen molecule degradation; and (c) degrades the fibronectin and laminin in the extracellular matrix facilitating cell sliding and healing.

It has been speculated that plasmin might generate chemotactic factors for polymorphonuclear neutrophils from the complement system and cause the formation of vasoactive kinins, which result in the increased entrance of serum antiproteases into the corneal stroma.

Epithelium, keratocytes and polymorphonuclear neutrophils of ulcerating corneas are capable of releasing uPA. Ulcerated corneas are typically caused by such things as puncture- or scrape-type injuries, etc. to the eye; they can also result from severe bacterial infections. Corneal haze is therefore not to be confused with an ulcerated cornea.

Urokinase was discovered in human urine in the early 1950s and was named urokinase or urinary Pg (plasminogen) activator (uPA). Both high and low molecular weight forms of uPA are available commercially. Urokinase is commercially available from a number of suppliers and manufacturers, including Abbott Laboratories, Inc. and Sterling Winthrop, Inc., under trade names ABBOKINASE™ (powder, lyophilized 250,000 IU/vial w/25 mg mannitol, 250 mg human albumin, 50 mg NaCl, preservative free in vials), BREOKINASE™, WIN-KINASE™, WIN-22005™, ACTOSOLV™, PERSOLV™, PUROCHIN™, UKIDAN™, and URONASE™. The predominant form of uPA in urinary preparations is 50,000 MW, whereas a truncated form (MW-about 33,000) is isolated from long-term cell culture. Lung and kidney are the richest normal sources of uPA. Low molecular weight (33,000) uPA is used clinically in the treatment of pulmonary embolism, acute myocardial infarction and other thrombotic diseases. The zymogen of uPA known as proUK is available as a recombinant protein and it has been shown to have thrombolytic activity.

uPA is immunologically distinct from tPA which was originally discovered in melanoma cells and it (tPA) has a molecular weight of 64,000–70,000. tpA is a product of vascular endothelial cells from a wide variety of tissues. tPA's mode of action is to bind to the surface of a blood clot. Plasminogen then binds to the tPA, with the presence of fibronectin enhancing the affinity of tPA for plasminogen by nearly 1,000 fold. Plasminogen activation to plasmin by tPA is potentiated by clot formation and further by partial clot degradation. tPA is used therapeutically as an antithrombolytic agent.

Streptokinase (SK) also named streptococcal fibrinolysin, is another plasminogen activator. SK is a species specific, monomeric protein, MW 47,000. SK does not have enzymatic activity by itself but by forming a 1:1 complex with human plasminogen, SK generates an active site on the Pg moiety to activate a second molecule of Pg forming two plasmin molecules. During the catalysis of plasminogen complexed to SK, SK undergoes proteolytic degradation resulting in a smaller (MW=36,000) but still active fragment.

Several published studies have related plasminogen activator levels to various forms of wound healing. EP-A-0 227 400 describes that topically administered tissue plasminogen activator (tPA) inhibits post-surgical adhesion formation which is a major post-surgical complication. It is stated that the use of tPA is not associated with the wound healing itself. Adhesion formation is a process occurring inside the body, predominantly in cavities, that is not related to the healing of the external wound as such EP 0 943 332 A1, Prevention and treatment of adhesions, discloses that increased synthesis or secretion of plasminogen activators prevents adhesions.

EP-A-0 261 599, discloses a diverse group of compositions for topical application, including preparations comprising tPA that are recommended for the treatment of heart attack victims.

Pharmacological treatment of open wounds using intravascular administration of thrombolytic agents, e.g., streptokinase, urokinase plasminogen activator (u-PA), and tissue-type plasminogen activator (tPA) has been reported Chester J., Darmandy J. A. In: *Leg ulcers diagnosis and treatment*. Westerhof W., ed. *Amsterdam: Elsevier* 1993, pp. 313–324. The use of topical tissue plasminogen activator (tPA) in wound healing was tested in U.S. Pat. No. 6,033, 664, Verheigen, Mar. 7, 2000; and related patent U.S. Pat. No. 5,925,350, entitled Use of preparation comprising a plasminogen activator to improve wound healing. The examples in the Verheigen patents are limited exclusively to leg ulcers treated with tPA. Application of plasminogen activators to the eye was neither tested nor mentioned, and only tissue plasminogen activator (tPA) was used. Verheigen discloses that topical application of plasminogen activators including urokinase is effective in the treatment of "persistent, or therapy resistant leg ulcers, bedsores, open burns and other slow- or non-healing wounds caused by many types of trauma, infection by micro-organisms, cancer and many other insults to the skin and tissue." Column 1, lines 12–15. The wounds studied in Verheigen are therefore very different and easily distinguishable from corneal haze following many weeks after laser surgery or other corneal injuries.

For example, "Ulcer" is defined in Dorland's Medical Dictionary, $26^{th}$ edition as "a local defect, or excavation, of the surface of an organ or tissue, which is produced by the sloughing of inflammatory necrotic tissue." The leg ulcers studied by Verheigen are highly inflamed (thus also highly vascularized) and they slough necrotic cells. By contrast, the healthy cornea is not vascularized because it must be transparent for proper vision, and inflammation (increased vascularization) of the cornea is not a common postoperative complication of laser surgery. The eye is capable of developing ulcers that fit the definition in Dorland, however, such ulcers are not an expected outcome on the cornea following laser eye surgery, and if they develop, a clinician would never confuse them with haze. PRK is a delicate procedure in which a region of the cornea 5–6 mm in diameter is treated with the laser, and corneal tissue is evenly and uniformly removed to a depth of 10–100 microns of tissue across the entire 5–6 mm corneal surface which is about 500 microns thick prior to the surgery. The injury to the cornea after PRK is not classified as a corneal ulcer because, for example, there is no irregular "excavation" or gouged out crater of tissue. Therefore, the teachings of Verheigen using tPA to promote wound healing of a highly vascularized leg ulcer are not predictive of the use of a plasminogen activator, whether tPA or urokinase, to treat or prevent haze from developing in the cornea weeks or months after laser surgery.

Canadian Application 2095207 filed in 1992, Schuler, et al. The use of inhibitors of plasminogen activators for the treatment of inflammations and wound, discloses and claims the use of inhibitors of plasminogen activators as a therapy "for inflammations of the eye and opacities of the eye, for example after laser treatment, [and] normal ophthalmic surgery . . . " (Schuler, et al., page 4, lines 15–32). They report an increase in plasmin activity in the lacrimal (tear) fluid after damage to the cornea, (Schuler, et al., page 1, lines 15–18), and they speculate that plasmin initiates a series of events that result in the breakdown of collagen molecules. Specifically, they found that plasminogen activator inhibitors block neovascularization and thereby restore the transparency of the cornea after inflammation. (page 8, lines 4–13.)

Others have speculated that plasmin might stimulate the replication of endothelial cells thus promoting angiogenesis (the proliferation of blood vessels), which has been shown to be an important factor in tissue repair. [Barlati S, Marchina E, Quaranta C A, Vigasio F, Semeraro F. *Analysis of fibronectin, plasminogen activators and plasminogen in tear fluid as markers of corneal damage and repair. Exp Eye Res.* 1990;51:1–9.] Plasmin inhibitors have been used to treat certain diseases associated with increased plasmin activity, but they are disadvantageous because of their toxic effects. (Schuler, et al., page 1, lines 23–35). Also, plasmin inhibitors, plasminogen activator inhibitors and combinations of these in conjunction with a variety of corticosteroids have been suggested as a means of minimizing degradation, and tissue removal due to plasmin-activity during the healing of laser refractive surgeries. [Lohmann C P, Marshall J. *Plasmin- and plasminogen-activator inhibitors after excimer laser photorefractive keratectomy: new concept in prevention of postoperative myopic regression and haze. Refract Corneal Surg* 1993;9:300–301.]

Plasminogen activator applied topically to the cornea is tolerated at very high levels for substantial periods of time. In a previous study, rabbit corneas were perfused in vitro for three hours with solutions containing urokinase in concentrations as high as 5,000 IU/ml. These experiments demonstrated that urokinase at concentrations up to 5,000 IU/ml is non-toxic to rabbit corneal endothelium, does not induce meaningful swelling of rabbit corneas, and retains a normal endothelial mosaic under scanning electron microscopic scrutiny. [Hull D S, Green K. *Effect of urokinase on corneal endothelium. Arch Ophthalmol* 1980;98:1285–1286.]

It has now been discovered that low levels of uPA in tear fluid for the first one to five days following laser surgery, specifically PRK, in both humans and rabbits correlates consistently with the development of postoperative haze weeks or months later. Thus, the present invention provides a method for reducing or preventing haze following laser surgery, by delivering a therapeutically effective amount of one or more plasminogen activators to the cornea immediately following surgery and for about up to the first twelve days after the procedure. The present invention is also directed to a topical ophthalmic composition for preventing or reducing haze following laser surgery, containing a therapeutically effective amount of one or more plasminogen activators formulated in a physiologically acceptable carrier suitable for ophthalmic use. The plasminogen activators that can be used in the present methods and compositions include most preferably urokinase, and also urokinase mutants, prourokinase, and prourokinase mutants. The methods and compositions of the present invention are also intended for use to reduce or prevent haze following other ophthalmic surgeries or resulting as a complication of ophthalmic diseases or eye injuries.

Figure 2:
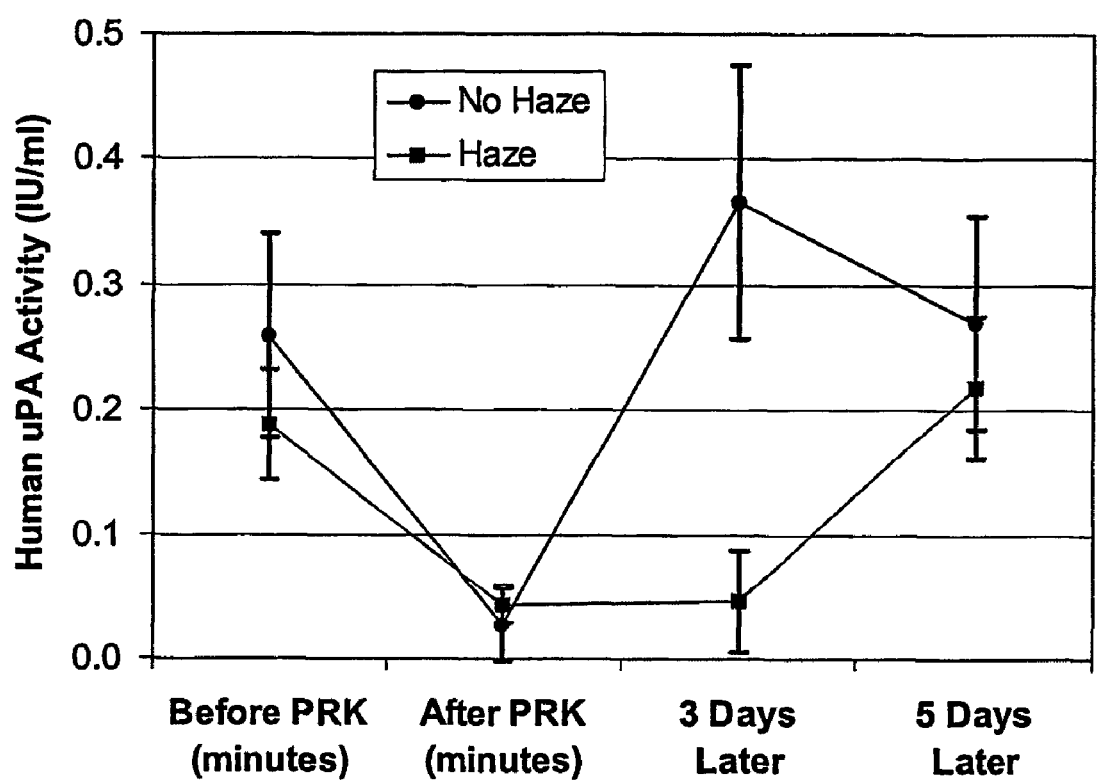
FIG. 2. Observed mean uPA activity in human tears following PRK: 71 eyes had normal uPA pattern and had no haze; 6 eyes had low mean uPA levels through the third day after PRK and all developed haze.

Examples 1 and 2 detailed below show that there is a pattern of uPA production in tears following PRK in both humans and in rabbits. In the human study, a distinct pattern of uPA levels in tears was seen following PRK that distinguished those patients that healed normally from those that developed haze. Mean uPA levels in tears dropped dramatically immediately following surgery for all patients, whether they developed haze or healed normally: there was a mean decrease of 90% in the 71 eyes that healed normally and a mean decrease of 77% in the 6 eyes that developed haze compared to the mean preoperative value for all 77 eyes tested. Example 1, FIGS. 1 and 2. Patient eyes that healed normally showed significantly elevated mean uPA levels compared to preoperative level (41% increase) on the third postoperative day, and levels returned to the preoperative levels by the fifth postoperative day. In sharp contrast to normal cases, mean tear uPA levels remained suppressed (76% below the preoperative mean) through the third postoperative day in all (six) cases that developed haze (Grade 1–2) three to six months post surgery [hereafter "haze-complicated cases"]. FIGS. 1 and 2. By the fifth postoperative day mean uPA levels in each haze-complicated eye were up 16% above mean preoperative levels, compared to a 41% increase by day three in normal eyes. Mean uPA levels of the two groups are distinctly separated on the third postoperative day with the mean uPA levels in the group developing haze being lower (statistically significant) than the mean of the normal group. FIG. 2. Individual values of the uPA levels for individual eyes of the normal and haze-complicated cases are shown in FIG. 1 and in Table 3 in Example 1.

Figure 3:
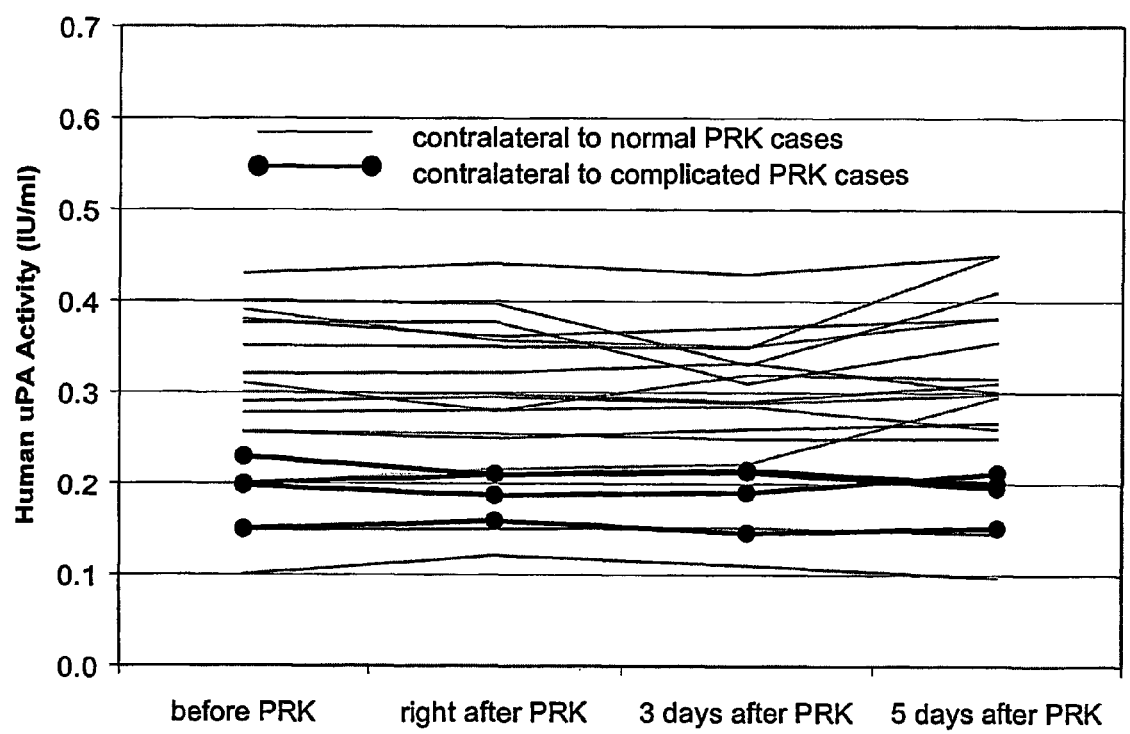
FIG. 3. Individual uPA activity levels in human tears are given for each contralateral unoperated eye during the study, before and after PRK was performed on the contralateral eyes that healed normally and the contralateral eyes that developed postoperative haze.

Haze-complicated eyes accounted for 8% (6/77) of the eyes that underwent PRK Haze was determined using the criteria set forth in Hanna K D, Pouliquen Y M, Savoldelli M et al. *Corneal wound healing in monkeys* 18 *months after excimer laser photorefractive keratectomy. Refract Corneal Surg.* 1990;6:340–345. Mean uPA levels for normal and haze-complicated cases overlap at the other three measurement times, preoperative day 0, and days 1 and 5. The control eyes that did not undergo PRK showed no appreciable change in uPA levels over the five-day period. FIG. 3. The results of this experiment show that extended suppression of uPA in tears to levels about 25% of mean preoperative levels through the third postoperative day correlates with the future development of haze.

Six out of six retrospectively identified haze-complicated cases showed significantly lower uPA levels on postoperative day 3 compared to normal cases and 71 out of 71 remaining eyes showed no ensuing haze. Using the uPA level as a criterion for haze prediction corresponds to a sensitivity of 1.0 (proportion of haze predictions to actual haze cases) and a specificity of 1.0 (proportion of no-haze prediction to actual no-haze cases). If low (below 0.1 IU/ml) uPA levels on postoperative day three had been used to prospectively identify (predict) eyes that might develop wound healing abnormalities (haze), then six out of six cases would have given a valid prediction.

Haze following PRK does not need to be bilateral, though it can be. Three of the patients had one haze-complicated eye and one normal eye, one patient had two haze-complicated eyes, and one patient (who only volunteered one eye for sampling) had a haze-complicated eye. Where the contralateral "control" eye that was not subjected to PRK was measured, the tear fluid flow and uPA levels remained essentially constant throughout the study (FIG. 3). This implies that the PRK surgery and tear sampling have little collateral effect with respect to changes in tearing or fibrinolytic activity in the contralateral untreated eye.

In the three cases where both eyes underwent PRK, and where only one eye developed haze, it was observed that the preoperative uPA values for both eyes were significantly lower than the mean uPA levels in the normal groups (Table 3). Moreover, for each of the three patients in the haze-complicated group having one normal and one haze-complicated eye, the preoperative uPA value was even lower in the eye that developed haze. However, the ranges of uPA levels for the normal and haze-complicated groups are overlapping on the preoperative measurement (FIG. 1). Therefore, the normal and haze-complicated cases are not distinguishable on the basis of the preoperative uPA levels.

Tear fluid is an easily accessible medium for studying corneal wound healing. Only one reported study followed levels of uPA in tear fluid during the progression of corneal re-epithelization, and this was done in rabbits following anterior keratectomy. [van Setten G B, Salonen E M, Vaheri A, et al. *Plasmin and plasminogen activator activities in tear fluid during corneal wound healing after anterior keratectomy. Curr Eye Res.* 1989;8:1293–1298.] Van Stetten et al. observed a statistically significant drop in urokinase levels on day 1 following anterior keretectomy (day 0=the day of the procedure). By days 2–3, uPA levels had returned to normal. The pattern of uPA levels in tears observed in the rabbit following anterior keratectomy is qualitatively similar to the pattern observed in normal human cases following PRK. All eleven rabbit eyes in the van Stetten study healed without haze (although haze is known to occur in rabbits after keratectomy), and they had a mean (±SEM) preoperative uPA level of 2.0 (±0.6) IU/ml that fell to a mean of 0.3 (±0.1) IU/ml postoperatively on day 1, and then rose to 2.1 (±0.3) IU/ml by days 2–3. The parallel pattern of uPA values in tears between humans and rabbits that healed normally after keratectomy, strengthens the conclusion that there is a "normal" pattern of UPA in tears that correlates positively with healing and normal, healthy corneal re-epithelization.

The van Stetten et al. rabbit study also measured tear fluid flow rates in addition to uPA levels. The tear fluid flow was found to increase after anterior keratectomy by a factor of 2.3 compared to preoperative flow. Therefore, dilution of plasminogen activator could be offered as a possible explanation for the drop in postoperative plasminogen activator level. However, the levels of uPA did not change by the dilution factor of 2.3: the postoperative drop in plasminogen activator was a factor of 6.7 over preoperative levels. Therefore, dilution alone is not a sufficient mechanism to explain the drop in plasminogen activator level. In the present work, the tear fluid flow measured in humans remained in the range of 5–15 µl/min for all eyes over all sample times, showing that the lowered uPA levels seen post-PRK in the examples below are not due to changes in tear fluid flow rates.

Although the exact mechanisms underlying post-PRK corneal healing complications are unknown, it is generally suspected that individual variations in corneal wound healing play a significant role in post-PRK refractive regression and haze formation. [Moller-Pedersen T, Li H F, Petroll W M, Cavanagh H D, Jester J V. *Confocal microscopic characterization of wound repair after photorefractive keratectomy. Invest Ophthalmol Vis Sci.* 1998;39:487–501]. The studies reported in Example 1 show that low uPA levels in tears sustained over a period of three days in humans cause the eventual development of haze.

Figure 4:
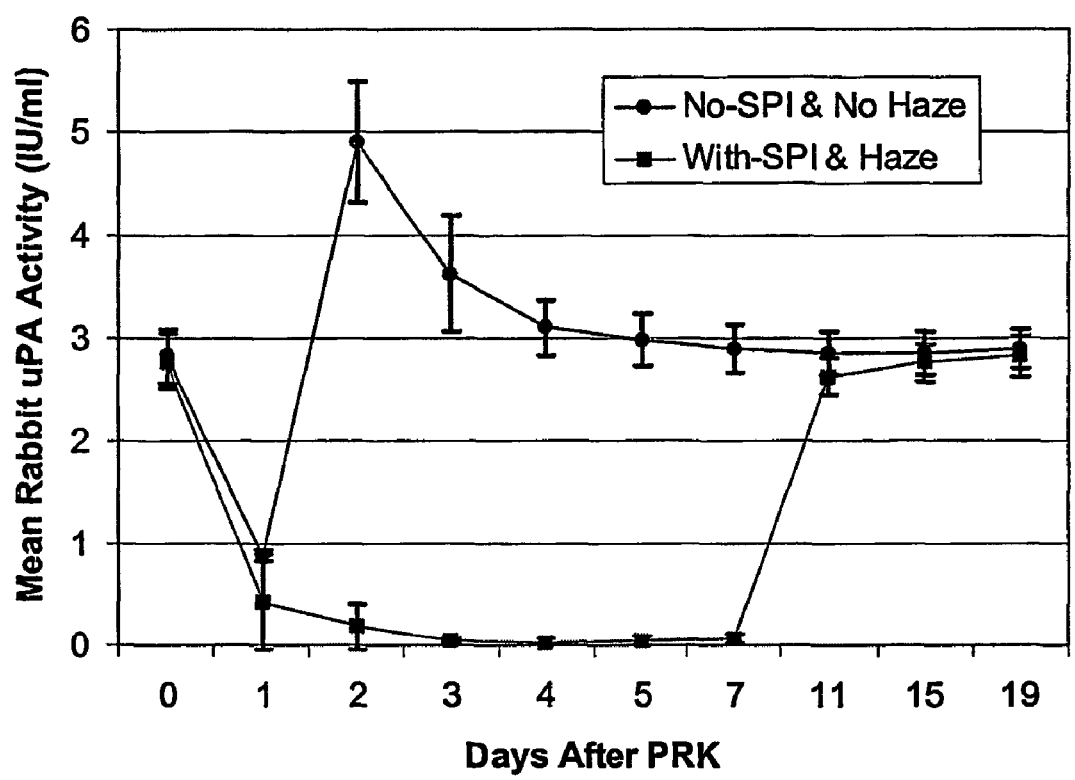
FIG. 4. Observed mean uPA in rabbit tears following PRK for eyes that were not treated (No-SPI) and for treated eyes (With-SPI). The 8 No-SPI eyes had a normal uPA activity pattern and none developed haze. The 8 SPI-treated eyes had suppressed uPA activity levels caused by treatment with SPI for seven days following PRK, and all developed postoperative haze.
Figure 5:
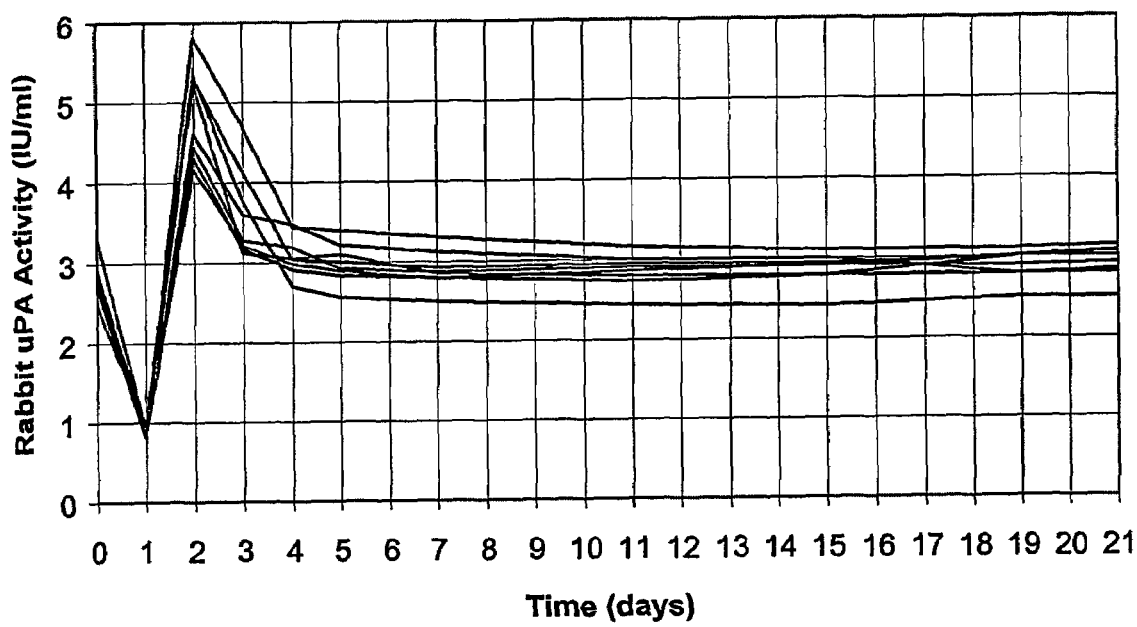
FIG. 5. Individual uPA activity levels in rabbit tears for eyes not treated with serine protease inhibitors (No-SPI) following PRK.

Example 2 shows that inhibition of uPA in tears in rabbits for seven days following PRK caused the formation of postoperative haze in all cases. Both eyes in each of 8 rabbits underwent PRK treatment; one eye of each rabbit was treated with the serine protease inhibitor (SPI) aprotinin on postoperative days 1–7 to inactivate uPA in the tears and on the surface of the cornea. Aprotinin is especially effective for inhibiting urokinase. Measurements of uPA were always made in the morning of the indicated day prior to treatment with SPI. The eight control eyes (No-SPI) showed uPA values that were significantly lower on day 1 and significantly higher on days 2 and 3 than the equilibrium preoperative values ($p<0.001$). FIGS. 4 and 5. uPA levels returned to preoperative equilibrium levels by postoperative day 4. FIGS. 4 and 5. The corneas remained clear in each of these SPI-untreated eyes throughout the 21 day study.

Figure 6:
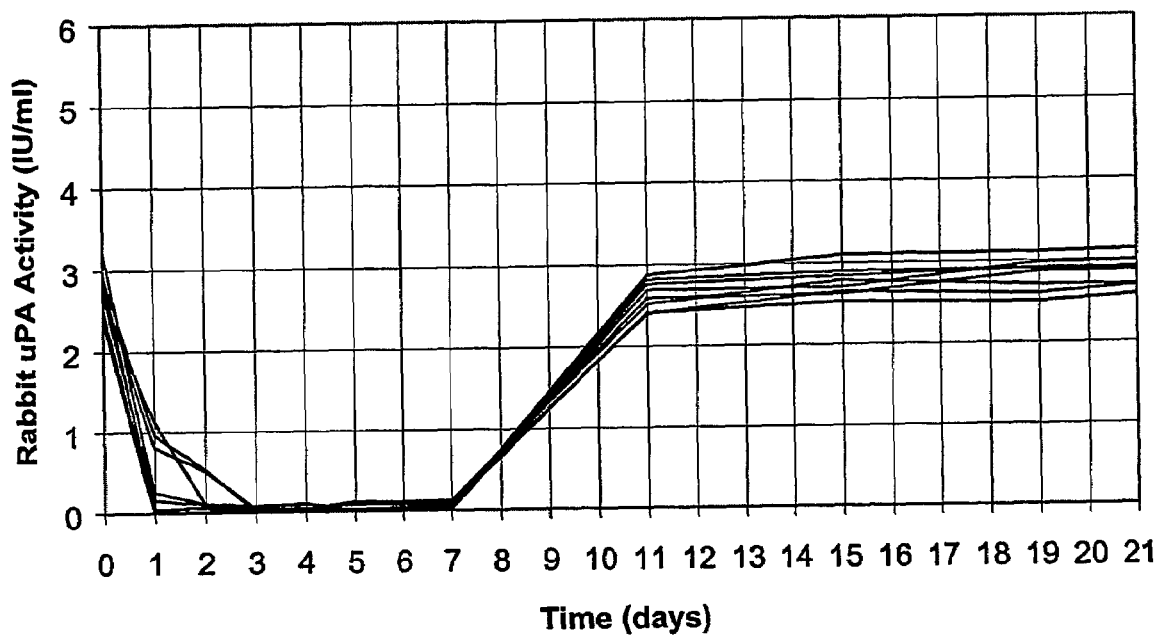
FIG. 6. Individual uPA activity levels in rabbit tears for eyes treated with serine protease inhibitors (With-SPI) for seven days following PRK.

The 8 contralateral SPI-treated eyes initially behaved like the untreated eyes in that they also showed post-PRK uPA values that were significantly lower than the preoperative equilibrium uPA levels ($p<0.001$) on day 1. The levels of uPA were intentionally suppressed with SPI for the first seven days following PRK. All 8 of these SPI-treated eyes had extremely low levels of uPA (approaching zero) and all developed corneal haze after about two months. FIGS. 4 and 6. The difference between the equilibrium UPA for the two groups of eyes after 19 days was not significant ($p=0.06$). These results show that postoperative corneal haze develops in rabbit eyes after PRK when uPA levels fall below preoperative equilibrium levels and approach zero by postoperative days 2–3 and remain suppressed during the first week following PRK. The human and rabbit studies together show that maintenance of uPA levels in tears and on the surface of the cornea at least at levels at or above the preoperative equilibrium mean for at least the first three or four days following PRK is necessary to prevent postoperative haze from developing.

Figure 7:
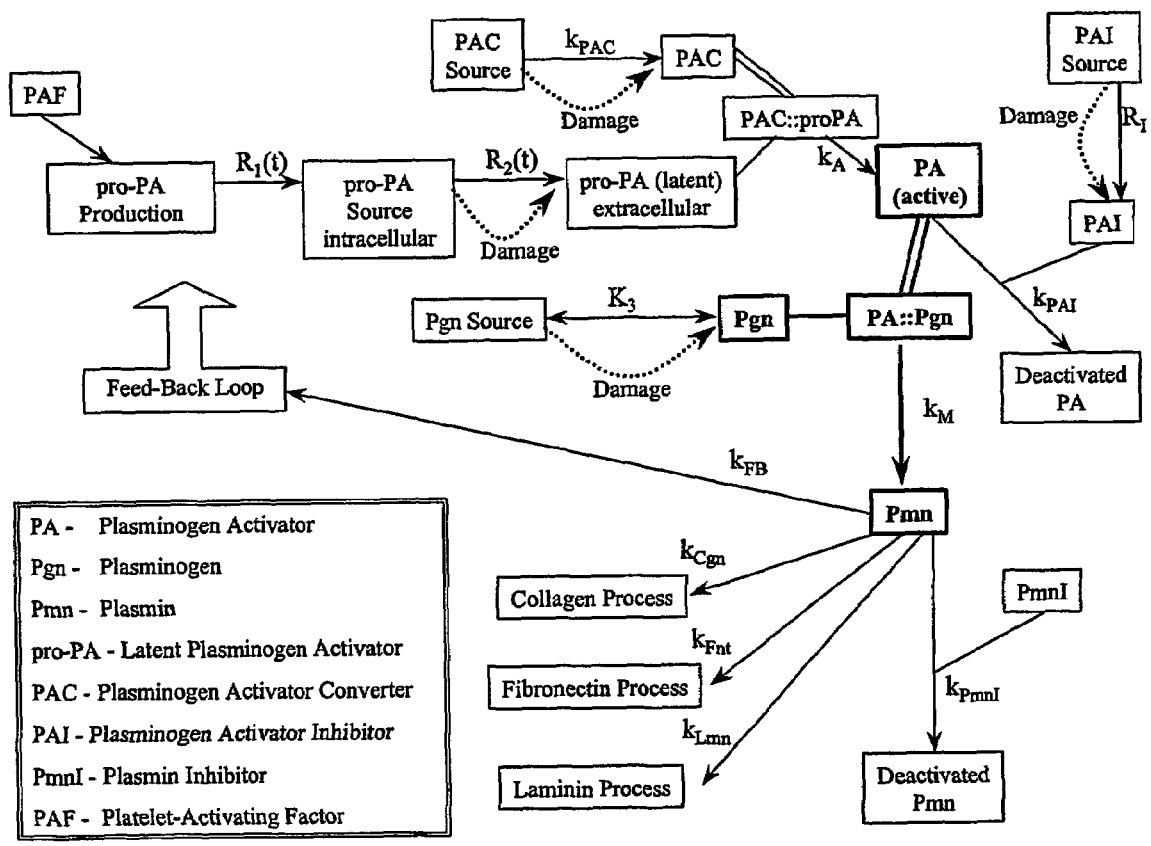
FIG. 7. Schematic diagram of the plasminogen activator to plasmin reaction system, showing the principle reaction in heavy lines, normal supporting reactions in light lines and damage mechanisms in dotted lines.

Example 3 describes a chemical kinetic model that has been constructed, FIG. 7, detailing changes in plasminogen activator activity during corneal wounding and wound healing that is consistent with measurements of uPA and plasmin in tear fluid after laser refractive surgery. Chemical reaction mechanisms and kinetics have been applied to the biochemical processes and materials accompanying corneal wounding. Comparisons have been made with measurements of uPA activity in human and rabbit tears following photorefractive keratectomy. Upon wounding, corneal epithelial cells release a surge of chemicals. The rate equations yield mathematical solutions in which the plasminogen activator rapidly reacts with plasminogen to form plasmin, and with plasminogen activator inhibitor to diminish the plasminogen activator level. Consistent with the measurements, these processes are rapid enough (within seconds) to elevate plasmin to a higher level and to deplete plasminogen activator to a lower level than preoperative levels prior to the time measurements are made, within minutes after surgery. The balance between plasminogen activator production and plasminogen activator inhibitor levels determines the course of plasminogen activator activity over the next few days. The equations then show a route toward return to preoperative equilibrium levels. Plasminogen activator activity levels measured in the tears of corneal wound cases are consistent with this chemical kinetic mechanism explaining the post-wound pattern of uPA activity.

In the critical period after corneal wounding, PA activity is governed by the ratio of the rate of production of PA to the rate of inhibition of PA. In the human experiments, where PA activity was found to be low over the first three days after PRK, FIGS. 1 and 2, haze developed after a few months. Subjecting post-PRK rabbit eyes to a PA inhibitor (serine proteinase inhibitor), FIGS. 4 and 6, also induced haze after a few months. The administration of PA on a therapeutic basis at a high enough concentration to mimic the natural physiological PA activity during the post-PRK period of several days to a week, FIGS. 1, 2, 4 and 5, is expected to establish and maintain the normal chemical kinetic balance, leading to normal healthy wound healing and the absence of haze.

The present invention provides a method for preventing or reducing corneal subepithelial haze following laser surgery, and other eye surgery, injury or disease that is associated with the formation of haze. A topical ophthalmic preparation containing one or more plasminogen activators, preferably uPA, is applied to the affected eye following the surgery or injury or disease, at a level to at least mimic normal physiologic levels of uPA present in the tears of eyes not undergoing any surgery, disorder or disease. The therapeutically effective level of uPA preferred for use in the present method ranges from about 0.1 to 2,500 IU/ml. Most preferred is 0.1–1.0 IU/ml; another preferred range is 1–10 IU/ml. The concentration of plasminogen activators that can be used in the ophthalmic compositions of the present invention, similarly ranges from about 0.1 to 2,500 IU/ml, most preferably about 0.1 to 1.0 IU/ml; with another preferred range of 1–10 IU/ml. In unusual circumstances, for example, should a patient display significant tearing following surgery that could wash away significant amounts of the topical plasminogen activator, higher concentrations may be required, for example from 10–100 IU/ml.

In one embodiment, the plasminogen activator(s) for use in the present inventions is applied topically to the surface of the eye about eight to twelve times on the day of surgery or injury starting immediately after surgery or injury, and four to eight times per day for each of the next six to twelve days thereafter. In a preferred embodiment, compositions having from about 0.1–1.0 IU/ml plasminogen activator formulated for topical composition are applied about twelve times per day (for example, every hour during wakefulness)

on day 1 starting immediately after laser surgery or injury to the eye, and five times per day, (every two hours) on postoperative days 2–7. The frequency of administration and concentration of plasminogen activator may be varied depending on a patient's history. For example, if a patient has particularly low pre-surgery plasminogen activator levels in tears, then application may need to be more frequent. In another embodiment, higher doses, for example 1–10 IU/ml or 10–100 IU/ml are applied less frequently following surgery or injury: for example, nine times per day during wakefulness on the day of surgery, and four times per day on postoperative days 2–7. Although doses as high as 2,500 IU/ml have been shown to be nontoxic to the cornea in vitro [Lohmann, C. P. et al., *Refractive & Corneal Surgery*, Vol. 9, July/August, 1993, page 300–302], such high doses are not envisioned for normal use, but may be required for patients with unusually high tear rates or where frequent application is impractical. The amount of uPA in the pharmacological preparations should be reduced or discontinued should the patient display inflammation, ulcers or other signs of adverse reaction. The pharmaceutical composition might be applied as single medication or combined with other useful medications, such as vasoconstrictors, antibiotics, etc.

Plasminogen activator(s) which may be used in accordance with the present invention include (pro-)urokinase, urokinase, streptokinase, and variants or mutants thereof constructed by, e.g., recombinant DNA technology, glycosylation variants, hybrid-proteins constructed from or containing parts of urokinase. uPA is the most preferred plasminogen activator, and more than one plasminogen activators can be applied simultaneously or included in the compositions. Preferably, plasminogen activators of mammalian origin are used.

Suitable uPA's and pro-uPA's have, e.g., been described in Hussain et al., *Arch Biochem. Biophys.* 220 (1983) 31–38; Stump et al., *Purification and characterization of single chain urokinase type plasminogen activator from human cell cultures*, J. Biol. Chem. 261 (1986) 1274–1278; Winkler et al. *Purification and characterization of recombinant urokinase from Escherichia coli*, Bio/Technology, 3 (1985) 992–1000; Wun et al., *Isolation and characterization of urokinase from human plasma*, J. Biol. Chem. 257 (1982); WP-81/01417 and EP-A-0 139 447.

The methods and compositions of the present invention are also intended for use to reduce or prevent haze following other ophthalmic surgeries or resulting as a complication of ophthalmic diseases or eye injuries including by way of example: normal ophthalmic surgery such as vitrectomy, cataract surgery, extracapsular cataract extraction, lens operations, lens replacement, lens implantation, keratoplasty, and corneal transplantations. Also included is haze that may follow conjunctivitis, keratoconjunctivitis, keratoconjunctivities sicca, iritis, iridocyclitis, keratitis, vasculitis, and uveitis.

Wound healing modulators, used alone or in combination in the compositions of the present invention, include: steroids, growth factors, basement membrane components, anti-oxidants, regulators of collagen structure, aldose reductase inhibitors (ARIs) nonsteroidal antiinflammatories (NSAIs), immunomodulators, antiallergics, fatty acid derivatives and antimicrobials.

It has been reported that corneal haze may be prevented with varying degrees of success with steroids, growth factors, basement membrane components, regulators of collagen structure, aldose reductase inhibitors, NSAIs, antioxidants, immunomodulators and antiallergics (which are particularly effective against corneal haze resulting from wound repair); growth factors, immunomodulators, anti-allergics and basement membrane components (which are particularly effective when fibroblasts of the stroma have been improperly activated); growth factors, steroids, immunomodulators, basement membrane components and anti-oxidants (which are particularly effective in alleviating the formation of corneal haze due to damaged collagen fibrils); growth factors and fatty acid derivatives of the arachidonic acid cascade (which are particularly effective when damaged or dead fibroblasts are present); and growth factors, steroids, NSAIs, antiallergics, anti-oxidants, aldose reductase inhibitors and antimicrobials (which are particularly effective in treating corneal haze attributable to edema). [Canadian patent application 2,095,207, issued to Schuler et al.] In further studies, the synthetic inhibitor of metalloproteinase was reported to reduce corneal haze by controlling the synthesis of type III collagen. [Chang J H, Kook M C, Lee J H, Chung H, Wee W R. *Effects of synthetic inhibitor of metalloproteinase and cyclosporin A on corneal haze after excimer laser photorefractive keratectomy in rabbits. Exp Eye Res* 1998;66:389–396.] In addition, mitomycin C, an alkylating agent with antineoplastic and antibiotic activities, has been reported to reduce haze after PRK by suppressing keratocyte proliferation. [Xu H, Liu S, Xia X, Huang P, Wang P, Wu X. *Mitomycin C reduces haze formation in rabbits after excimer laser photorefractive keratectomy. J Refract Surg* 2001;17:342–349.] To the extent that these compounds do not interfere with the plasminogen activators, they may be included in the compositions of the present inventions.

In addition to the principal active ingredients, the compositions of the present invention may further comprise various formulatory ingredients, such as antimicrobial preservatives and tonicity agents. For example, antimicrobial preservatives include: benzalkonium chloride, thimerosal, chlorobutanol, methylparaben, propylparaben, phenylethyl alcohol, EDTA, sorbic acid, POLYQUAD and other agents equally well known to those skilled in the art. Such preservatives, if employed, will typically be used in an amount between about 0.0001 wt. % and about 1.0 wt. %. Suitable agents which may be used to adjust tonicity or osmolality of the compositions include: sodium chloride, potassium chloride, mannitol, dextrose glycerine and propylene glycol. If used, such agents will be employed in an amount between about 0.1 wt. % and about 10.0 wt. %; however, preferable compositions of the present invention will not include preservatives or tonicity agents which are known to adversely affect or irritate the eye, particularly the cornea.

Elevation of intraocular pressure may occur during and following photoablation of the cornea. Control of intraocular pressure contributes to the health of the cornea thereby allowing the cornea to heal without resulting complications including corneal haze. Adjuncts for controlling intraocular pressure which may be included in the compositions of the present invention include antihypertensive agents such as, for example, latanoprost, apraclonidine, timolol, betaxolol, levobunalol, glycerin, isosorbide, manitol, urea, paraminoclonidines, epinephrine and carbonic anhydrase inhibitors. The compounds can be topically applied to the eye following photoablation at concentrations between about 0.1 and about 2.0 wt. % preferably about 0.5 wt. %. In addition, miotics can be used to control intraocular pressure, For example miotics such as carbachol, pilocarpine, physostigmine, echothiophate and isofluorphate can be used.

Humectants may be used prior to, during and after photoablation of the cornea and may be included optionally in the compositions of the present invention. These adjuncts promote healing of the cornea by providing lubrication and preserving the natural tear physiology. Humectants can include preparations which typically comprise hydroxyethylcellulose, hydroxypropylcellulose, hydroxypropylmethylcellulose, methylcellulose, polyvinyl alcohol, cellulose esters, povidone or other suitable polymeric systems.

Epithelial cell health promoters as used herein, are compounds known to contribute to the health of the epithelial cells of the cornea. The presence of these compounds prior to, during, and/or after photoablation of the cornea can contribute to the prevention of corneal haze by encouraging the rapid resumption of epithelial integrity and prevention of stromal edema. Epithelial cell health promoters which can be used optionally as adjuncts with the compositions of the present invention can include: ascorbic acid; retinoids, such as retinoic acid, retinol, retinal and retinoyl .beta.-glucuronide; aloe vera; collagenase inhibitors; and elastase inhibitors.

uPA can be topically applied to the cornea in eye drops or salve, ointment cream, emulsion, suspension or liposome preparation suitable for ophthalmic use. Aqueous solutions of the plasminogen activator are preferred for topical application to the eyes. Many examples of suitable compositions for topical application of an active substance are known in the art. Preferably such a pharmaceutical composition is sterile or aseptic and can be packaged in tubes, bottles or other containers suitable for easy topical application.

In the foregoing specification, the invention has been described with reference to specific embodiments thereof. It will, however, be evident that various modifications and changes may be made to the inventions without departing from the broader spirit and scope of the invention. The present application will be described in further detail, while referring to the following non-limiting examples.

3. EXAMPLE 1

Quantification of the Changes of uPA Levels in Human Tear Fluid During Corneal Re-epithelialization After Excimer Laser PRK.

Materials and Methods Forty-two patients (26 female, 16 male) undergoing PRK surgery, between the ages of 17 to 51 years (mean: 27; SD: 9 years), were selected for this study after obtaining informed consent in adherence to the Declaration of Helsinki. For a given patient, the PRK was performed one eye at a time with an interval of one to two weeks between surgeries. Both PRK eyes were sampled except for seven patients (3 female, 4 male), who volunteered for sampling from only one eye. Excluded from consideration were patients from whom a 15 µl tear sample could not be obtained within three minutes. For 20 of the surgeries where additional informed consent could be obtained, the contralateral eye was sampled as a "control" eye. This gave a sample population of 77 eyes (41 right, 36 left) and 20 contralateral control eyes. Preoperative mean refractive error was −3.0 diopters (SD: 3.0, range: 5.0 to −10.0 diopters). Eighteen of the eyes had preoperative astigmatism (mean: −1.5, SD: 0.6, range: −1.0 to −2.75 cylinder). Seventeen of the patients had previous usage of contact lenses (mean usage: 4, SD: 2, range: 1 to 9 years).

PRK treatments using the Schwind Keratom II ArF excimer laser (193 nm) were performed by the same surgeon at Vital-Laser LLC, Department of Ophthalmology, University Medical School of Debrecen. De-epithelialization was performed with a blunt Keratome Blade knife after epithelial marking with a 6.0–6.5 mm Hoffer trephine for spherical correction and 7.5–8.0 mm for astigmatic correction centered over the pupil. The epithelium was scraped gently from periphery to center, paying attention not to damage the surface of Bowman's layer. Residual epithelial debris was removed with a sterile microsponge. Epithelial anesthesia was induced using 0.4% oxybuprocaine hydrochloride eye drops. The diameter of the ablation zone was 6.1 mm (SD: 0.2, range: 6.0 to 6.5 mm) for patients without astigmatism. For astigmatic patients, the diameter of the astigmatic ablation mask was 7.5 mm (SD: 0.6, range: 6.0 to 8.1 mm) and the spherical ablation mask was 5.7 mm (SD: 0.1, range: 5.3 to 6.0 mm). The mean ablation depth of the PRK surgery was 48 microns (SD: 22, range: 12 to 120 microns). The mean ablation depth (47 microns) of the subgroup without astigmatism was not statistically significantly different (p >0.66) from the mean ablation depth (50 microns) of the astigmatic subgroup. The postoperative treatment included antibiotic eye drops, CILOXAN™ (Alcon), hourly on the first postoperative day, and five times daily during the next five days for each patient. The eye drops were withdrawn for at least 8 hours before tear sampling to avoid the possibility of tear sample dilution.

After the five day period, FLUCON™ (Alcon) and TEARS NATURALE™ (Alcon) were given 5 times daily during the first month, reduced to 4 times daily for the second month and to 3 times daily for the third month. No other treatment was used during this period. All patients received follow-up examinations at 1,3 and 6 months following the PRK procedure.

Tear samples for uPA analyses were obtained immediately before and immediately after the PRK treatment, and on the third and fifth postoperative days from the PRK eye and the contralateral eye where it was used. Samples consisted of tears collected with glass capillaries [Tözsér J, Berta A, Punyiczki M. *Plasminogen activator activity and plasminogen independent amidolytic activity in tear fluid from healthy persons and patients with anterior segment inflammation. Clin Chim Acta.* 1989;183:323–331; and van Haeringen N J, Glasius E. *The origin of some enzymes in tear fluid, determined by comparative investigations with two collection methods. Exp Eye Res.* 1976;22:267–272] under slit lamp illumination from the lower tear meniscus (a horizontal thickening of the precorneal tear film by the lower margin) at the lateral canthus. Care was taken not to touch the conjunctiva. The same collection method was used throughout the study. The duration of the sampling time was recorded and the secretion rate was calculated in µl/min, dividing the obtained tear volume by the time of sample collection. Samples used in this investigation had secretion rates of 5–15 µl/min for both the PRK eyes and the contralateral controls. Samples were centrifuged (1800 rpm) for 8–10 minutes right after sample collection and supernatants were deep-frozen at −80° C. and were thawed only once for measurements.

uPA levels were measured in the sample tears by a spectrophotometric method using human plasminogen and a plasmin-specific chromogenic peptide substrate, D-valyl-L-leucyl-L-lysine-p-nitroanilide (S-2251). Shimada H, Mori T, Takada A et al. *Use of chromogenic substrate S-2251 for determination of plasminogen activator in rat ovaries. Thrombos Haemostas (Stuttgart).* 1981;46:507–510. This assay is sensitive predominantly to urokinase-like plasminogen activator. [Tözsér J, Berta A, Punyiczki M. *Plasminogen activator activity and plasminogen independent amidolytic activity in tear fluid from healthy persons and patients with anterior segment inflammation. Clin Chim*

*Acta.* 1989;183:323–331.] Plasminogen and the S-2251 were purchased from Chromogenix (Mölndal, Sweden). Urokinase standard was purchased from Choay (Paris, France). This assay is suitable to measure plasmin activity but can also be used for determining UPA levels by adding plasminogen to the reagents. uPA levels were measured as described by Shimada et al. with the following modifications according to Tözsér and co-workers [özsér J, Berta A, Punyiczki M. *Plasminogen activator activity and plasminogen independent amidolytic activity in tear fluid from healthy persons and patients with anterior segment inflammation. Clin Chim Acta.* 1989;183:323–331; and Tözsér J, Berta A. *Urokinase-type plasminogen activator in rabbit tears. Comparison with human tears. Exp Eye Res.* 1990; 51:33–37]: 5 µl tear, or standard urokinase, or plasmin was incubated in 100 µl of 0.05 Tris buffer, pH 7.4, at 37° C. in the presence of 0.5 mmol/l chromogenic substrate S-2251 and 1 µmol/l human plasminogen in wells of microtiter plates. After 4 hours incubation, the reaction was terminated by the addition of 500 µl of 8 mol/l acetic acid. The absorption was measured at 405 nm with a Labsystem Multiscan MS spectrophotometer. Plasminogen independent amidolytic activity was measured similarly but plasminogen was omitted from the incubation mixture.

The absorption difference between the values obtained with and without plasminogen was considered to be due to the uPA levels in tear, while the absorbance value obtained without plasminogen was considered as plasminogen independent amidolytic activity. Based on the absorption values gained in the same system with urokinase standard solutions with different concentrations, a calibration curve was generated. The uPA levels of the measured samples were calculated with this calibration curve and were expressed in IU/ml urokinase equivalent values. Plasminogen independent activity was found to be negligible in all of the tear samples.

Determination of haze was made without any knowledge of the uPA levels for any of the patients. Hence there was no bias in the determination of haze or in the correlation of uPA levels with haze. The haze grading system of Hanna was adopted. [Hanna K D, Pouliquen Y M, Savoldelli M et al. *Corneal wound healing in monkeys 18 months after excimer laser photorefractive keratectomy. Refract Corneal Surg.* 1990;6:340–345].

Standard statistical procedures were used to compare patient characteristics between different groups (t-test for means of correlated pairs). uPA levels were compared between different groups using t-tests for means with equal variances. Comparisons with control eyes were performed using paired t-tests. Differences having probability levels, p, less than 0.05 are considered significant, and p<0.001 is considered highly significant.

Results: During the five day period of tear sampling for each eye, there were no clinical features that distinguished any of the eyes. However, six of the PRK treated eyes (five patients: 4 female, 1 male) developed mild to marked subepithelial corneal haze (grade 1 to 2) between the third and sixth month, accompanied simultaneously by a slight decrease in visual acuity. These six eyes were retrospectively labeled "complicated" cases and represent an 8% (6 out of 77) frequency of occurrence. The remaining cases did not exhibit visual complications and were retrospectively designated "normal" cases. Three of the patients had one "complicated" and one "normal" eye; one patient had two "complicated" eyes; and one of the patients with a "complicated" eye had volunteered only one eye for sampling.

Individual values of the uPA for each eye of the normal and haze-complicated groups are shown in FIG. 1, mean values are in FIG. 2. The plasminogen activator activities of the two groups are distinctly separated on the third postoperative day and overlap at the other three measurement times. FIG. 3 shows the individual values of the plasminogen activator activities for all of the contralateral eyes that did not undergo PRK. Patient characteristics are provided in Table 1.

TABLE 1

Characteristics of patients: mean (SD), number of patients, N, and significance levels, p, for t-test comparison between normal and complicated cases.

|  | Age (years) | Contact Lenses (years) |
| --- | --- | --- |
| Normal | 27 (9) | 4 (2) |
| N | 40 | 15 |
| Complicated | 23 (5) | 5 (2) |
| N | 5 | 4 |
| p (normal vs. complicated) | 0.38 | 0.35 |

TABLE 2

Visual and surgical characteristics: mean (SD), number of eyes, N, and significance levels, p, for t-test comparisons between normal and complicated cases.

|  | Pre-PRK Astigmatism (cylinder) | Pre-PRK Refraction (diopters) | Ablation Depth (microns) |
| --- | --- | --- | --- |
| Normal | −1.6 (0.6) | −2.9 (3.1) | 47 (22) |
| N | 16 | 71 | 71 |
| Complicated | −1.0 (0.0) | −5.1 (1.3) | 57 (23) |
| N | 2 | 6 | 6 |
| p (normal vs. complicated) | 0.24 | 0.08 | 0.33 | uPA levels (IU/ml): mean (SD), number of eyes, N, and significance levels, p, for t-test comparison between normal, haze-complicated and normal contralateral cases.

There are no statistically significant differences in age, length of contact lens wear, prior refractive correction, or extent of astigmatism between the two groups. The uPA mean values for the normal and haze-complicated cases are compared in Table 3. With respect to the uPA measurements, the normal cases established a pattern in which there is (1) a drop in the mean value of uPA to about 11% of the preoperative mean level immediately after the PRK treatment, (2) followed by an increase of 41% above the preoperative level by the third postoperative day, and (3) a return to within 4% of the preoperative level by the fifth postoperative day. There was no significant difference (p=0.15) between the preoperative mean uPA levels and the value on the fifth postoperative day in normal patients. However, the mean uPA values immediately after and on the third postoperative day were significantly lower and greater, respectively, (p<0.001) than the preoperative and five-day postoperative mean uPA levels. A very different pattern of uPA values is seen for the haze-complicated cases.

Table 3 During the postoperative period for the six haze-complicated cases, the mean uPA value decreased to only 23% of the preoperative mean value immediately after the PRK treatment. Instead of increasing dramatically (41%) above the preoperative levels on day 3 as was observed in Normal cases. The mean uPA values immediately after PRK and on the third postoperative day were not significantly different (p=0.81) from one another and each was significantly less (p<0.001) than the preoperative mean uPA value. By the fifth day, the mean uPA level was 16% above the preoperative mean value in haze complicated cases. In addition, there was a significant increase (p=0.02) in mean uPA levels on the fifth postoperative day compared to the preoperative mean value. This may represent a rebound phenomenon where the eye is trying to compensate for the low levels of uPA on days 1–3. These results show a 100% positive correlation between suppressed uPA levels immediately after surgery and through at least day three, and development of haze.

TABLE 3

Plasminogen activator activities (IU/ml): mean (SD), number of eyes, N, and significance levels, p, for t-test comparison between normal, complicated and contralateral cases.

| Condition | Pre-PRK | Post-PRK | Post-PRK + 3 Days | Post-PRK + 5 Days |
|---|---|---|---|---|
| Normal | 0.259 | 0.027 | 0.366 | 0.269 |
| (N = 71) | (0.082) | (0.029) | (0.109) | (0.085) |
| Complicated | 0.188 | 0.043 | 0.046 | 0.218 |
| (N = 6) | (0.045) | (0.015) | (0.041) | (0.056) |
| Contralateral Normal | 0.299 | 0.297 | 0.290 | 0.310 |
| (N = 16) | (0.092) | (0.086) | (0.080) | (0.097) |
| Contralateral Complicated | 0.195 | 0.192 | 0.191 | 0.190 |
| (N = 4) | (0.033) | (0.024) | (0.032) | (0.027) |
| p (normal vs. complicated) | 0.04 | 0.21 | <0.001 | 0.15 |
| p (contralateral. normal vs. normal) | 0.74 | <0.001 | 0.002 | 0.87 |
| p (contralateral compl. vs. compl.) | 0.49 | <0.001 | 0.006 | 0.83 |

The preoperative mean value is significantly lower (p=0.04) for the haze-complicated cases than the corresponding normal uPA mean value. However, due to overlap of preoperative means, the preoperative levels of uPA cannot be used to predict which patients will develop haze. The uPA mean value for the haze-complicated case versus the normal cases on the third post-operative day is highly significant (p<0.001).

uPA mean levels for the contralateral eyes are shown in Table 3. The mean uPA levels (normal group: 0.299±0.087 IU/ml; haze-complicated group: 0.192±0.026 IU/ml) remained steady over the five day measurement period. (FIG. 3). The mean change in value for the normal group over five days was 0.019±0.023 IU/ml; for the haze-complicated group: 0.011±0.007 IU/ml. The mean uPA levels in the contralateral haze-complicated cases were significantly lower (p<0.001) than the corresponding mean levels of the contralateral normal eyes. uPA levels in both contralateral eye groups were significantly different than the PRK-treated eyes immediately after and three days after surgery.

The results of these studies show that patients with suppressed levels (less than 0.1 IU/ml) of uPA in tear fluid (below preoperative levels of about 0.1–0.45 IU/ml) in the first three to five days following PRK all develop haze at some time during the six months following the procedure.

4. EXAMPLE 2

Inhibition of uPA in Rabbit Tears Following PRK Results in the Formation of Haze.

Both eyes in each of 8 rabbits underwent PRK treatment. One eye of each rabbit was treated with a serine protease inhibitor (SPI) over the first 7 days to inactivate uPA in the tears and on the surface of the cornea. uPA in the tear samples was measured by a spectrophotometric method using human plasminogen and chromogenic peptide substrate S-2251.

Materials and Methods Sixteen eyes of eight normal healthy New Zealand rabbits (3.0–3.5 kg) underwent PRK surgery for spherical correction using the Schwind Keratom II ArF excimer laser (193 nm), performed by the same surgeon at Vital-Laser LLC, Department of Ophthalmology, University Medical School of Debrecen. Animals were handled and treated in adherence to the ARVO Statement for the Use of Animals in Ophthalmic and Vision Research. De-epithelialization was performed with a blunt Keratome Blade knife after epithelial marking with a 6.0–6.5 mm Hoffer trephine. The epithelium was scraped gently from periphery to center. Residual epithelial debris was removed with a sterile microsponge.

Topical anesthetic (0.4% oxybuprocaine hydrochloride) eye drops were administered twice before the surgery. General anesthesia was accomplished by intravenous injection of ketamine-xylazine (2.2:1 ratio, 10 mg/kg). The PRK surgeries were performed on the morning of day 1. The postoperative treatment included antibiotic eye drops, Ciloxan (Alcon), twelve times (hourly) on day 1 and five times (every two hours) on five additional days (postoperative days 2–5 and 7). FLUCON™ (Alcon) and TEARS NATURALE™ (Alcon) were given 5 times daily (every two hours) during the first postoperative month, reduced to 4 times daily (every three hours) for the second month and 3 times daily (every four hours) for the third month. All rabbits received follow-up examinations at 1, 3 and 6 months following the PRK procedure.

In addition, the left eye of each rabbit received 1 drop of 10,000 KIE/ml serine protease inhibitor (SPI), aprotinin (Gordox, Richter Gideon Rt., Budapest), twelve times (hourly) on day 1 and five times (every two hours) on five additional days (postoperative days 2–5 and 7). This was designated the "With-SPI" group. The right eyes were not treated with SPI and were designated the "No-SPI" group. After the seventh day, identical treatment was used on both eyes. No other treatment was used during the six month follow-up period. SPI is an effective inhibitor of plasminogen activator activity, consistent with the known inhibitory affinity of aprotinin for urokinase-type plasminogen activator. Lottenberg R, Sjak-Shie N, Fazleabas A T, Roberts R M. *Aprotinin inhibits urokinase but not tissue-type plasminogen activator.* Thromb Res 1988;49:549–556; and Fritz H, Wunderer G. *Biochemistry and applications of aprotinin, the kallikrein inhibitor from bovine organs.* Arzneim Forsch 1983;33:479–494.

Tear samples for plasminogen activator activity analyses were obtained on the day before the PRK surgery (day 0). Tear samples were collected within minutes after PRK (day 1), before treatment with any eye drops. Daily on postoperative days 2–5, on postoperative day 7 and every fourth day thereafter for three months (91 days), tears were sampled in the morning prior to the administration of any eye drops on the given day so that SPI treatment would not change the uPA levels.

Samples consisted of tears collected with glass capillaries using i.m. injection of pilocarpine hydrochloride (5 mg/kg) for stimulation. Tears were taken from the lower tear meniscus and care was taken not to touch the conjunctiva. The same collection method was used throughout the study. The duration of the sampling time was recorded and the secretion rate was calculated in μl/min, dividing the obtained tear volume by the time of sample collection. Samples used in this investigation had secretion rates of 15–50 μl/min. Samples were centrifuged (1800 rpm) for 8–10 minutes right after sample collection and supernatants were immediately deep-frozen at −80° C. and were thawed only once for measurements.

Plasminogen activator activity was measured in the sample tears by a spectrophotometric method using human plasminogen and a plasmin-specific chromogenic peptide substrate, D-valyl-L-leucyl-L-lysine-p-nitroanilide (S-2251). This assay is sensitive predominantly to urokinase-type plasminogen activator. Plasminogen and the S-2251 were purchased from Chromogenix (Milan, Italy). Urokinase standard was purchased from Choay (Paris, France). This assay is suitable to measure plasmin activity but can also be used for determining plasminogen activator activity by adding plasminogen to the reagents. Plasminogen activator activity was measured as described by Shimada and coworkers with the modifications of Tözsér and co-workers as in Example 1. Determination of haze was made without any knowledge of the plasminogen activator levels for any of the rabbits. The haze grading system of Hanna was adopted.

Standard statistical procedures were used to compare plasminogen activator activities within and between different groups using t-tests for means with unequal variances and paired t-tests to compare results on contralateral eyes. Differences having probability, p, less than 0.05 are considered significant, and p<0.001 is considered highly significant.

Results FIGS. 4 and 5 show the time course of uPA levels over the first 21 days after PRK for the No-SPI rabbit eyes. Table 4 gives mean values of the plasminogen activator activity for the early measurement days and the average uPA activity for days 19–91. In Table 4 and the Figures, "day 0" represents the day before PRK surgery, "day 1" is the day of the surgery, and the succeeding days follow. The mean plasminogen activator activity value before surgery (day 0) was not significantly different (p=0.16) than the 19–91 day equilibrium plasminogen activator activity level. The mean uPA levels were significantly (p<0.001) lower on day 1 (about 69%), and higher on days 2 and 3 (about 74% and 28%, respectively) than the mean equilibrium plasminogen activator activity level. The plasminogen activator activity on day 4 was significantly (p=0.02) higher (10%) than the equilibrium level, but from day 5 and beyond, there were no significant differences with the equilibrium value. The corneas remained clear in these eyes over the six-month follow-up period.

Table 4. Mean values (SD) and comparison of plasminogen activity in rabbits tears after PRK for No-SPI With SPI groups (significant difference when p<0.05).

TABLE 4

Mean values (SD) and comparison of plasminogen activator activity in rabbit tears after PRK for the No-SPI and With-SPI groups (significant difference when p < 0.05)

| Day | PAA: No-SPI IU/ml | PAA: With-SPI IU/ml | PAA Comparison No-SPI vs With-SPI p |
|---|---|---|---|
| 0 | 2.82 (0.26) | 2.77 (0.26) | 0.46 |
| 1 | 0.87 (0.06) | 0.42 (0.47) | 0.03 |
| 2 | 4.90 (0.60 | 0.18 (0.21) | <0.001 |
| 3 | 3.62 (0.56) | 0.04 (0.03) | <0.001 |
| 4 | 3.10 (0.26) | 0.03 (0.04) | <0.001 |
| 5 | 2.99 (0.25) | 0.05 (0.05) | <0.001 |
| 7 | 2.89 (0.24) | 0.05 (0.04) | <0.001 |

TABLE 4-continued

Mean values (SD) and comparison of plasminogen activator activity in rabbit tears after PRK for the No-SPI and With-SPI groups (significant difference when p < 0.05)

| Day | PAA: No-SPI IU/ml | PAA: With-SPI IU/ml | PAA Comparison No-SPI vs With-SPI p |
|---|---|---|---|
| 11 | 2.86 (0.21) | 2.63 (0.18) | 0.009 |
| 15 | 2.86 (0.21) | 2.76 (0.18) | 0.06 |
| 19–91 | 2.93 (0.20) | 2.88 (0.22) | 0.06 |

FIGS. 4 and 6 show the first 21 days of plasminogen activator activity for the contralateral With-SPI eyes. Individual mean plasminogen activator activity levels for various measurement days are given in Table 4. SPI suppressed uPA activity to a mean value averaged over days 1–7 of 0.13 (0.15) IU/ml. The mean plasminogen activator activity prior to surgery (day 0) was not significantly different (p=0.18) than the equilibrium plasminogen activator activity level of 2.88 (0.22) IU/ml, averaged over days 19–91. Mean uPA activity of SPI-treated eyes on days 1–7 (corresponding to the period of SPI-suppression) was significantly (p<0.001) lower than the equilibrium plasminogen activator activity level (95%). Mean uPA levels remained low from day seven through day eleven, only returning to preoperative levels by day 15. All 8 of these SPI-treated eyes developed corneal haze after two months.

The difference between the presurgical (day 0) mean plasminogen activator activities for the two groups was not significant (p=0.46) nor was the equilibrium (days 19–91) mean plasminogen activator activity significantly different (p=0.06) for the two groups.

In summary, for normal rabbit eyes (No-SPI) there is a drop in uPA activity after surgery (day 1) that is followed by an overshoot to a level above the initial plasminogen activator activity on day 2 and lasting for a few days. Finally, there is a return to the initial plasminogen activator activity level which was maintained from days 19–91. This pattern of plasminogen activator activity seen in FIGS. 4 and 5 for the No-SPI group resembles the pattern seen for humans who experience normal wound healing without the occurrence of haze. In humans, the plasminogen activator activity fell to a level near zero after PRK, then rose above initial levels on postoperative day 3 and returned to the initial level by postoperative day 5. The plasminogen activator activity pattern in FIGS. 4 and 5 is also consistent with that reported by van Stetten for rabbits with normal wound healing following anterior keratectomy.

In contrast, the plasminogen activator activity pattern shown in FIGS. 4 and 6 for the With-SPI group was intentionally lowered following PRK to resemble the pattern found in humans who presented abnormal wound healing and experienced haze. In the human abnormal healing case, the plasminogen activator activity fell to near zero after PRK and remained low through the third postoperative day. By the fifth postoperative day, the plasminogen activator activity was beyond but returning to the initial level. Here, the plasminogen activator activity level was deliberately suppressed using SPI in the With-SPI group of rabbit eyes over a period of seven days, as shown in FIGS. 4 and 6. uPA levels returned to normal preoperative levels by day fifteen.

These results show that uPA must be maintained at least at the natural physiological levels or elevated significantly above preoperative levels for the first 3–4 days following PRK in rabbits in order to prevent the eventual development of corneal haze. A return to normal uPA preoperative levels from days 19–91 was not sufficient to prevent postoperative haze. Thus, there is a rather short, critical window following surgery or injury to the cornea when uPA levels must be elevated to prevent haze from forming.

5. EXAMPLE 3

Chemical Kinetic Model of Plasminogen Activator and the Wound Healing Process Following Photorefractive Keratectomy Biochemical mechanisms A schematic chemical kinetic mechanism of the plasminogen activator-plasmin reaction system is presented in FIG. 7. Some reactions are considered to be active all the time (indicated by solid lines and arrows), while other processes only occur when the cornea has been damaged (indicated by dashed lines). FIG. 7 also contains a list of definitions of abbreviated terms. A summary of the interdependent rate equations and their known properties follows.

A latent form of plasminogen activator, pro-plasminogen activator (pro-PA), is present in cultures of rabbit corneal epithelial cells or normal corneas. The pro-PA is converted into the active form of plasminogen activator (PA) by a converter enzyme, here denoted by plasminogen activator converter (PAC). The conversion reaction is written in Equation (1).

(1)

indicating an overall forward rate constant $k_A$ and ignoring an intermediate enzyme-substrate complex. A number of different enzymes can convert pro-PA to its activated form, including trypsin, plasmin, kallikrein, elastase, and cathepsin B.

Platelet-activating factor (PAF) induces urokinase-type plasminogen activator mRNA expression in the corneal epithelium by signaling a phosphorylation pathway. It is assumed that the pro-PA production process proceeds at the rate $R_1(t)$ to produce intracellular pro-PA that accumulates as a pro-PA source indicated in Equation (2).

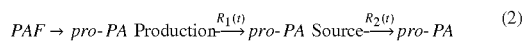

(2)

Further, it is assumed that corneal epithelial cells release pro-PA under normal circumstances at a rate designated $R_2(t)$. Both $R_1(t)$ and $R_2(t)$ are written as functions of time, t; that is, the rates can change with time and circumstances. If there is damage to the cell, $R_2(t)$ comes very large, equivalent to releasing the stored pro-PA and giving an impulse of pro-PA into the extracellular space.

Plasminogen (Pgn) circulates in the blood and is present in the cornea. It is assumed to be pervasive and therefore to be in equilibrium with its source. The release equilibrium is symbolically designated $K_3$ in Equation (3).

(3)

The principal reaction of interest here is between PA and Pgn to form plasmin (Pmn) in an enzymic process with the forward rate $k_M$ shown in Equation (4).

(4)

PA can be inhibited by type 1 or type 2 inhibitors that are released after trauma from epithelial cells of the cornea and conjunctiva. The plasminogen activator inhibitor (PAI) reacts with PA at a rate $k_{PAI}$ given in Equation (5).

(5)

Pmn can participate in a variety of processes: collagen, fibronectin and laminin degradation, and feedback interactions to produce more plasminogen activator. Also, Pmn can be inhibited with plasmin inhibitor (PmnI), such as $\alpha_2$-antiplasmin. These degradation, feedback and inhibition processes are designated here as X, with corresponding rate constants $k_X$, where X is any one of these processes as shown symbolically in Equation (6).

$$Pmn + X \xrightarrow{k_X} Process_X \qquad (6)$$

Experimental plasminogen activator and plasmin levels Levels of uPA in humans and rabbits relative to photorefractive keratectomy have been determined before surgery after surgery and later in the healing process. The measured values are shown in FIGS. 1, 2, 4 and 5. The magnitude of the uPA level is not identical between humans and rabbits, but the time course for uPA qualitatively follows the same trend for both species as seen in the Figures.

Preoperative equilibrium rate equations In the time prior to corneal surgery or wounding, there is an equilibrium situation pertaining to the molecules: pro-PA, PA, Pgn, and Pmn. In the absence of cell damage, the reactions in Equations (1)-(6) occur and give rise to the rate Equations (7)–(9).

$$\frac{\partial [pro\text{-}PA]}{\partial t} = R_2(t) - k_A[pro\text{-}PA][PAC] \qquad (7)$$

$$\frac{\partial [PA]}{\partial t} = k_A[pro\text{-}PA][PAC] - k_{PAI}[PA][PAI] \qquad (8)$$

$$\frac{\partial [Pmn]}{\partial t} = k_M[PA][Pgn] = \sum k_X[Pmn][X] \qquad (9)$$

where the brackets in these and the following equations signify concentration. The principal molecules take on equilibrium concentration values as indicated in Equations (10) –(15) which are a consequence of the kinetic equations. These equations describe equilibrium between the different constituents. The equilibrium concentrations of each molecule in Equations (11)–(15) depend on the ratio of the pro-PA production rate, $R_2(eq)$, and the other rate constants and concentrations as indicated.

$$[PAC] \approx [PAC]_{eq} \qquad (10)$$

$$[PAI] \approx [PAI]_{eq} \qquad (11)$$

$$[Pgn] \approx [Pgn]_{eq} \qquad (12)$$

$$[pro\text{-}PA]_{eq} \approx \frac{R_2(eq)}{k_A[PAC]_{eq}} \qquad (13)$$

$$[PA]_{eq} \approx \frac{k_A[pro\text{-}PA]_{eq}[PAC]_{eq}}{k_A[PAI]_{eq}} \approx \frac{R_2(eq)}{k_{PAI}[PAI]_{eq}} \qquad (14)$$

$$[Pmn]_{eq} \approx \frac{k_A[pro\text{-}PA]_{eq}[PAC]_{eq}}{\sum k_X[X]_{eq}} \approx \frac{R_2(eq)}{\sum k_X[X]_{eq}} \qquad (15)$$

Corneal damage period Upon sustaining damage, corneal epithelial cells release pro-PA, PAC, PAI and Pgn as well as several other enzymes. In FIG. 7, the damage situation is shown symbolically with dotted lines circumventing the normal rate of pro-PA, PAC, PAI and Pgn release. This is tantamount to a sudden influx of these chemicals into the extracellular milieu. The concentrations of pro-PA, PAC, PAI and Pgn will change instantly from $[pro\text{-}PA]_{eq}$, $[PAC]_{eq}$, $[PAI]_{eq}$ and $[Pgn]_{eq}$ to new higher levels, $[pro\text{-}PA]_D$, $[PAC]_D$, $[PAI]_D$ and $[Pgn]_D$, respectively. Then the pro-PA will follow a first order exponential decrease in concentration over time, t, as shown in Equation (16).

$$[pro\text{-}PA]_t = [pro\text{-}PA]_D \exp\left\{-k_A \int [PAC]_D dt\right\} \qquad (16)$$

This converts the pro-PA into PA. The concentration of PA will have a tendency to increase as pro-PA decreases; this tendency follows the intuitive notion of an increase of PA concomitant with corneal cell damage. However, there is a further reaction that simultaneously decreases the PA concentration: namely, the inhibitor reaction with PAI shown in Equation (17).

$$\frac{\partial[PA]_t}{\partial t} = -\frac{\partial[pro\text{-}PA]_t}{\partial t} - k_{PAI}[PA]_t[PAI]_t \qquad (17)$$

The first term on the right side of this equation represents the increase in PA derived at the expense of pro-PA, and the second term is the inhibitor reaction. The latter reaction is first order in PA concentration and is accelerated at elevated PA concentrations. The PA must balance the opposing tendencies represented in Equation (17). The Pmn concentration will respond to the initial changes in the PA and Pgn concentrations by initially increasing because of the influence of the first term on the right side of Equation (18).

$$\frac{\partial[Pmn]_t}{\partial t} = k_M[PA]_t[Pgn]_D - \sum k_x[Pmn]_t[X]_t \qquad (18)$$

The several processes represented by the second term in Equation 18 are likely to be slow relative to the other reaction in Equation 18 and those in Equation 17, especially slow relative to the PAI inhibition in Equation 17.

Over the time frame of exponential decay indicated in Equation (16), the pro-PA level will drop from the concentration $[pro\text{-}PA]_D$ to a new level $[pro\text{-}PA]_{after}$ where the dominant term in Equation (7) becomes the first term on the right, which depends on the intracellular production of pro-PA. The pseudo-equilibrium value of the pro-PA will now again be governed by an equation like Equation (13) except modified as shown in Equation (19) where the production rate constant could be different than before, $R_2(eq) \neq R_2(after)$, and possibly lower due to depleted intracellular stores.

$$[pro\text{-}PA]_{after} \approx \frac{R_2(\text{after})}{k_A[PAC]_{after}} \qquad (19)$$

If the PAC concentration is at an elevated level, then both the $R_2(\text{after})$ and the $[PAC]_{after}$ will tend to lower the pro-PA level, $[pro\text{-}PA]_{after}$, below the former equilibrium value $[pro\text{-}PA]_{eq}$. The concentration of PA will adjust to a new equilibrium that includes the inhibitor reaction in Equation (20).

$$[PA]_{after} \approx \frac{k_A[pro\text{-}PA]_{after}[PAC]_{after}}{k_{PAI}[PAI]_{after}} \approx \frac{R_2(\text{after})}{k_{PAI}[PAI]_{after}} \qquad (20)$$

The PA concentration will change by the amount that $R_2(\text{after})$ and $[PAI]_{after}$ differ from their values in Equation (14). If the PAI concentration is at an elevated level, then both $R_2(\text{after})$ and the $[PAI]_{after}$ will tend to lower the PA level, $[PA]_{after}$, below the former equilibrium value $[PA]_{eq}$. A low level of $[PA]_{after}$ is consistent with both the human and rabbit measurements in the immediate post-surgical period. The Pmn concentration is determined through integration of Equation (18) over the time interval of the exponential decay of Equation (16), whereby an amount of Pgn is converted to Pmn that is equivalent to the amount of PA that was produced from the $[pro\text{-}PA]_D$ level. Since the measurements after surgery were performed immediately (within a few minutes) after the surgery, the rate of exponential decay in Equation (16) must be quite rapid (perhaps on a time scale of seconds), since the transformation to $[PA]_{after}$ and $[Pmn]_{after}$ occurs within that immediate (few minutes) time period. Conversion of pro-PA into PA (Eq. 16) in a time scale of seconds is consistent with previous in vitro kinetic measurements of this process in purified systems. [Camiolo S M, Thorsen S, Astrup T. *Fibrinogenolysis and fibrinolysis with tissue plasminogen activator, urolinase, streptokinase-activated human globulin, and plasmin.* Proc Soc Exper Biol Med 1971;138:277–280. Christensen U. *Kinetic studies of the urokinase-catalysed conversion of NH$_2$-terminal glutamic acid plasminogen to plasmin.* Biochim Biophys Acta 1977;481:638–647. Wohl R C, Summaria L, Arzadon L, Robbins K C. *Steady state kinetics of activation of human and bovine plasminogens by streptokinase and its equimolar complexes with various activated forms of human plasminogen.* J Biol Chem 1978;253:1402–1407. Collen D. *On the regulation and control of fibrinolysis.* Thrombos Haemostas (Stuttgart) 1980;43:77–89.]

Wound healing period Later in the wound healing process, the pro-PA production level is assumed to increase to an elevated level $R_1(\text{later})$ with an elevated release rate, $R_2(\text{later})$. These elevated rates of pro-PA production change the concentration of PA from the value shown in Equation (20) to an elevated level, $[PA]_{later}$. This is consistent with the elevated level of uPA observed in the human and rabbit experiments. These changes in uPA along with changes in the levels of PAC and PAI have repercussions on the Pmn concentration in this later stage. The balance of factors in Equation (18) must yield a reduction in the Pmn concentration during this later period.

Postoperative equilibrium period Finally, even later, the pro-PA production level should eventually return to the normal level, $R_1(eq)$ and the normal release rate, $R_2(eq)$. Also the PAC and PAI levels should return to normal. Thus a return to the preoperative levels designated [pro-PA]$_{eq}$, [PA]$_{eq}$ and [Pmn]$_{eq}$ should again be realized. This is consistent with the observed PA level in humans.

Discussion The sources of the molecules involved in the plasminogen activator-plasmin cascade are the various cells and structures in the cornea. The site of chemical interactions is also within the cornea, while the sampling site is the tear fluid. It is assumed that the transfer of molecules through mass transport from cornea to tear fluid is rapid and that the molecular concentrations are in equilibrium between the two.

The mechanism described in the present work involves known reactions of the constituents of the plasminogen activator-plasmin cascade following corneal wounding. The analysis provides the following qualitative approach to understanding this complex biochemical system. Under normal circumstances, equilibrium is established between the collection of molecules participating in the system. When corneal damage (surgery) occurs, pro-PA, PAC, PAI and Pgn are released instantly from wounded corneal epithelial cells. This leads to a rapid cascade (on a time scale of seconds) starting with the conversion of pro-PA to active PA and subsequent reaction of the PA with Pgn to form Pmn. In addition, the PA is exposed to elevated levels of PAI. By the time measurements are made after surgery (within a few minutes), PA is reduced to a low level by the PAI and Pmn is elevated. Although the PA level is reduced, production or release of PA becomes elevated to restore a depleted PA level and to accommodate a continued demand for Pmn. The balance between PA production and PAI levels determines the course of PA activity over the next few days. Then when cell damage is cleared (several days later), there is an overshoot of PA to an elevated level because of the elevated production. Later, by the fifth day, equilibrium is re-established.

PA activity levels measured in the tears of corneal wound cases with normal corneal healing are consistent with the chemical kinetic mechanism outlined in FIG. 7. This assumes a rapid release of chemicals from damaged corneal epithelial cells and a rapid cascade of reactions to form Pmn. Measurements made minutes after surgery are too late to observe the expected increase in PA following the corneal wound. The fast decay of PA causes the PA level to become low within minutes after surgery and to give rise to the observation of low PA. Thus, the chemical kinetic mechanism provides an explanation for the normal pattern of post-wound PA activity.

In the foregoing specification, the invention has been described with reference to specific embodiments. It will, however, be evident that various modifications and changes may be made without departing from the broader spirit and scope of the invention. The specification and drawings are, accordingly, to be regarded in an illustrative rather than a restrictive sense.

What is claimed is:

1. A topical ophthalmic composition for reducing corneal subepithelial haze, comprising a therapeutically effective amount of one or more urokinase-type plasminogen activators selected from the group comprising urokinase, urokinase mutants, streptokinase, and streptokinase mutants formulated in an ophthalmically acceptable carrier.

2. The topical ophthalmic composition of claim 1, wherein the therapeutically effective amount of urokinase-type plasminogen activator is from about 0.1–1.0 IU/ml.

3. The topical ophthalmic composition of claim 1, wherein the therapeutically effective amount of urokinase-type plasminogen activator is from about 1.0–10 IU/ml.

4. The composition of claim 1, wherein the urokinase-type plasminogen activator is urokinase.

5. The composition as in claim 1, wherein the urokinase-type plasminogen activator is streptokinase.

6. The topical ophthalmic composition of claim 1, wherein corneal subepithelial haze is the result of laser surgery, ophthalmic surgery or corneal injury.

7. The topical ophthalmic composition of claim 1, wherein the therapeutically effective amount of urokinase-type plasminogen activator is from about 10–100 IU/ml.

8. The method as in claim 1, wherein the one or more urokinase-type plasminogen activators are formulated in eye drops.

9. A method of reducing postoperative corneal subepithelial haze following laser surgery, comprising the topical application to the surface of the affected eye of a therapeutically effective amount of one or more urokinase-type plasminogen activators selected from the group comprising urokinase, urokinase mutants, streptokinase, and streptokinase mutants to reduce postoperative haze, wherein application of the urokinase-type plasminogen activator(s) begins the day of the surgery and is applied every day for at least the first five days after surgery.

10. The method of claim 9, wherein the laser surgery is photorefractive keratectomy.

11. The method of claim 9, wherein the laser surgery is laser in situ keratomileusis.

12. The method as in claim 9, wherein the urokinase-type plasminogen activator is urokinase.

13. The method as in claim 9, wherein the urokinase-type plasminogen activator is streptokinase.

14. The method as in claim 9, wherein the therapeutically effective amount of urokinase-type plasminogen activator is from about 0.1–10 IU/ml.

15. The method of claim 9, wherein the therapeutically effective amount of urokinase-type plasminogen activator is from about 1–10 IU/ml.

16. The method of claim 9, wherein the therapeutically effective amount of urokinase-type plasminogen activator is applied topically to the surface of the eye about eight to twelve times on the day of surgery starting immediately after surgery, and about four to eight times per day for each of the next six to twelve days thereafter.

17. The method of claim 9, wherein the therapeutically effective amount of urokinase-type plasminogen activator is applied topically to the surface of the eye every one to two hours for about the first twelve hours after surgery, and about every two to four hours to obtain between four and eight applications per day for the each of the next six to ten days thereafter.

18. The method of claim 9, wherein the therapeutically effective amount of urokinase-type plasminogen activator is from about 10–100 IU/ml.

* * * * *